(12) United States Patent
Wildman

(10) Patent No.: US 7,248,933 B2
(45) Date of Patent: Jul. 24, 2007

(54) ARTICLE LOCATING AND TRACKING SYSTEM

(75) Inventor: Timothy D. Wildman, Metamora, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 1099 days.

(21) Appl. No.: 10/141,457

(22) Filed: May 8, 2002

(65) Prior Publication Data

US 2002/0183979 A1 Dec. 5, 2002

Related U.S. Application Data

(60) Provisional application No. 60/289,432, filed on May 8, 2001.

(51) Int. Cl.
*G06N 5/00* (2006.01)

(52) U.S. Cl. .................. 700/90; 700/115; 701/213

(58) Field of Classification Search ............. 700/90, 700/115; 701/213
See application file for complete search history.

(56) References Cited

U.S. PATENT DOCUMENTS

| | | |
|---|---|---|
| 2,976,419 A | 3/1961 | Menke et al. |
| 3,439,320 A | 4/1969 | Ward |
| 3,478,344 A | 11/1969 | Schwitzgebel et al. |
| 3,696,384 A | 10/1972 | Lester |
| 3,714,573 A | 1/1973 | Grossman |
| 3,739,329 A | 6/1973 | Lester |
| 3,805,227 A | 4/1974 | Lester |
| 3,805,265 A | 4/1974 | Lester |
| 3,988,724 A | 10/1976 | Anderson |
| 4,151,407 A | 4/1979 | McBride et al. |

(Continued)

FOREIGN PATENT DOCUMENTS

| | | |
|---|---|---|
| GB | 0 193 359 | 2/1988 |
| GB | 2 230 365 | 10/1990 |
| GB | 2 265 018 | 1/1993 |
| WO | WO 92/09178 | 5/1992 |

OTHER PUBLICATIONS

"Great New Product: Infrared Locator," Teleconnect, Feb., 1986.

(Continued)

*Primary Examiner*—Wilbert L. Starks, Jr.
(74) *Attorney, Agent, or Firm*—Bose McKinney & Evans LLP

(57) ABSTRACT

A system for tracking an activity in a healthcare environment includes a master station having a processor, a memory, and a transceiver, badges coupled to objects, each transmitting a unique badge ID, and sensors disposed throughout the environment, each including a transceiver for receiving badge IDs and transmitting to the master station transceiver the badge IDs and a unique sensor ID that relates the sensor to a location. The master station processor determines object locations from the badge and sensor IDs by identifying the badge associated with the object, relating the sensor ID to the sensor location, and storing object location information in memory. Each badge also includes a displacement sensor that generates signals indicating object movement and direction for transmission to the sensor transceivers which forward displacement information to the master station. The master station processor uses the information to update the stored object location information.

87 Claims, 9 Drawing Sheets

U.S. PATENT DOCUMENTS

| | | |
|---|---|---|
| 4,216,462 A | 8/1980 | McGrath et al. |
| 4,225,953 A | 9/1980 | Simon et al. |
| 4,275,385 A | 6/1981 | White |
| 4,598,275 A | 7/1986 | Ross et al. |
| 4,601,064 A | 7/1986 | Shipley |
| 4,649,385 A | 3/1987 | Aires et al. |
| 4,706,689 A | 11/1987 | Man |
| 4,728,928 A | 3/1988 | Shipley |
| 4,740,792 A | 4/1988 | Sagey et al. |
| 4,837,568 A | 6/1989 | Snaper |
| 4,843,640 A | 6/1989 | Juengel |
| 4,885,571 A | 12/1989 | Pauley et al. |
| 4,955,000 A | 9/1990 | Nastrom |
| 4,967,195 A | 10/1990 | Shipley |
| 4,979,217 A | 12/1990 | Shipley |
| 4,981,141 A | 1/1991 | Segalowitz |
| 4,990,892 A | 2/1991 | Guest et al. |
| 5,012,113 A | 4/1991 | Valentine et al. |
| 5,014,040 A | 5/1991 | Weaver et al. |
| 5,027,314 A | 6/1991 | Linwood et al. |
| 5,036,852 A | 8/1991 | Leishman |
| 5,038,800 A | 8/1991 | Oba |
| 5,051,741 A | 9/1991 | Wesby |
| 5,062,151 A | 10/1991 | Shipley |
| 5,119,104 A | 6/1992 | Heller |
| 5,153,584 A | 10/1992 | Engira |
| 5,214,421 A | 5/1993 | Vernon et al. |
| 5,218,344 A | 6/1993 | Ricketts |
| 5,231,991 A | 8/1993 | Nelson |
| 5,245,314 A | 9/1993 | Kah, Jr. |
| 5,266,944 A | 11/1993 | Carroll et al. |
| 5,291,399 A | 3/1994 | Chaco |
| 5,317,309 A | 5/1994 | Vercellotti et al. |
| 5,319,191 A | 6/1994 | Crimmins |
| 5,319,363 A | 6/1994 | Welch et al. |
| 5,341,412 A | 8/1994 | Ramot et al. |
| 5,351,149 A | 9/1994 | Crimmins |
| 5,363,425 A | 11/1994 | Mufti et al. |
| 5,374,921 A | 12/1994 | Martin et al. |
| 5,387,993 A | 2/1995 | Heller et al. |
| 5,390,238 A | 2/1995 | Kirk et al. |
| 5,396,224 A | 3/1995 | Dukes et al. |
| 5,402,469 A | 3/1995 | Hopper et al. |
| 5,412,715 A | 5/1995 | Volpe |
| 5,417,222 A | 5/1995 | Dempsey et al. |
| 5,421,177 A | 6/1995 | Sieber et al. |
| 5,426,425 A | 6/1995 | Conrad et al. |
| RE35,035 E | 9/1995 | Shipley |
| 5,455,851 A | 10/1995 | Chaco et al. |
| 5,458,123 A | 10/1995 | Unger |
| 5,461,665 A | 10/1995 | Shur et al. |
| 5,465,082 A | 11/1995 | Chaco |
| 5,471,404 A | 11/1995 | Mazer |
| 5,493,283 A | 2/1996 | Hopper et al. |
| 5,504,477 A | 4/1996 | Whitright et al. |
| 5,515,426 A | 5/1996 | Yacenda et al. |
| 5,525,967 A | 6/1996 | Azizi et al. |
| 5,534,876 A | 7/1996 | Erickson et al. |
| 5,541,585 A | 7/1996 | Duhame et al. |
| 5,548,637 A | 8/1996 | Heller et al. |
| 5,561,412 A | 10/1996 | Novak et al. |
| 5,572,195 A | 11/1996 | Heller et al. |
| 5,572,653 A | 11/1996 | DeTemple et al. |
| 5,576,952 A | 11/1996 | Stutman et al. |
| 5,588,009 A | 12/1996 | Will |
| 5,589,821 A | 12/1996 | Sallen et al. |
| 5,590,648 A | 1/1997 | Mitchell et al. |
| 5,594,786 A | 1/1997 | Chaco et al. |
| 5,600,108 A | 2/1997 | Newham |
| 5,621,384 A | 4/1997 | Crimmins et al. |
| 5,627,524 A | 5/1997 | Fredrickson et al. |
| 5,629,678 A | 5/1997 | Gargano et al. |
| 5,633,742 A | 5/1997 | Shipley |
| 5,635,907 A | 6/1997 | Bernard et al. |
| 5,640,002 A | 6/1997 | Ruppert et al. |
| 5,640,157 A | 6/1997 | Langeraar |
| 5,652,570 A | 7/1997 | Lepkofker |
| 5,682,139 A | 10/1997 | Pradeep et al. |
| 5,682,142 A | 10/1997 | Loosmore et al. |
| 5,686,888 A | 11/1997 | Welles, II et al. |
| 5,689,229 A | 11/1997 | Chaco et al. |
| 5,714,932 A | 2/1998 | Castellon et al. |
| 5,729,196 A | 3/1998 | Aljadeff et al. |
| 5,731,757 A | 3/1998 | Layson, Jr. |
| 5,732,711 A | 3/1998 | Fitzpatrick et al. |
| 5,742,233 A | 4/1998 | Hoffman et al. |
| 5,745,037 A | 4/1998 | Guthrie et al. |
| 5,745,272 A | 4/1998 | Shipley |
| 5,748,084 A | 5/1998 | Isikoff |
| 5,748,148 A | 5/1998 | Heiser et al. |
| 5,751,246 A | 5/1998 | Hertel |
| 5,754,125 A | 5/1998 | Pearce |
| 5,760,687 A | 6/1998 | Cousy |
| 5,767,788 A | 6/1998 | Ness |
| 5,771,003 A | 6/1998 | Seymour |
| 5,793,861 A | 8/1998 | Haigh |
| 5,815,566 A | 9/1998 | Ramot et al. |
| 5,818,617 A | 10/1998 | Shipley |
| 5,822,418 A | 10/1998 | Yacenda et al. |
| 5,822,544 A | 10/1998 | Chaco et al. |
| 5,825,283 A | 10/1998 | Camhi |
| 5,828,306 A | 10/1998 | Curran |
| 5,831,533 A | 11/1998 | Kanno |
| 5,835,907 A | 11/1998 | Newman |
| 5,838,223 A | 11/1998 | Gallant et al. |
| 5,838,472 A | 11/1998 | Welch et al. |
| 5,920,287 A | 7/1999 | Belcher et al. |
| 6,009,333 A | 12/1999 | Chaco |
| 6,037,879 A | 3/2000 | Tuttle |
| 6,040,773 A | 3/2000 | Vega et al. |
| 6,091,332 A | 7/2000 | Eberhardt et al. |
| 6,097,301 A | 8/2000 | Tuttle |
| 6,100,804 A | 8/2000 | Brady et al. |
| 6,101,390 A | 8/2000 | Jayaraman et al. |
| 6,104,311 A | 8/2000 | Lastinger |
| 6,114,962 A | 9/2000 | Wiklof et al. |
| 6,118,379 A | 9/2000 | Kodukula et al. |
| 6,121,878 A | 9/2000 | Brady et al. |
| 6,127,928 A | 10/2000 | Issacman et al. |
| 6,130,612 A | 10/2000 | Castellano et al. |
| 6,131,067 A | 10/2000 | Girerd et al. |
| 6,133,832 A | 10/2000 | Winder et al. |
| 6,133,837 A | 10/2000 | Riley |
| 6,137,411 A | 10/2000 | Tyren |
| 6,137,412 A | 10/2000 | Herzer |
| 6,144,301 A | 11/2000 | Frieden |
| 6,147,592 A | 11/2000 | Ulrich et al. |
| 6,150,921 A | 11/2000 | Werb et al. |
| 6,154,139 A | 11/2000 | Heller |
| 6,177,861 B1 | 1/2001 | MacLellan et al. |
| 6,204,764 B1 | 3/2001 | Maloney |
| 6,204,765 B1 | 3/2001 | Brady et al. |
| 6,204,813 B1 | 3/2001 | Wadell et al. |
| 6,211,781 B1 | 4/2001 | McDonald |
| 6,252,512 B1 | 6/2001 | Riley |
| 6,259,355 B1 | 7/2001 | Chaco et al. |
| 6,344,794 B1 | 2/2002 | Ulrich et al. |
| 6,353,413 B1 | 3/2002 | White et al. |
| 6,375,612 B1 * | 4/2002 | Guichon et al. ............ 600/300 |
| 6,738,712 B1 * | 5/2004 | Hildebrant .................. 701/213 |
| 6,812,824 B1 * | 11/2004 | Goldinger et al. ......... 340/10.1 |
| 6,847,892 B2 * | 1/2005 | Zhou et al. ................. 701/213 |
| 6,901,304 B2 * | 5/2005 | Swan et al. ................. 700/115 |

2002/0057203 A1    5/2002    Borders et al.

OTHER PUBLICATIONS

T.H. Ooi, "Low Cost RF Identification and Locating System," IEEE Trans. On Consumer Electronics, vol. 35 No. 4, Nov. 1989, pp. 831-39

United Indentifications Systems Corp., Infra-Com, 1989.

The Computer for the 21$^{st}$ Century, mark Weiser, Scientific American, Sep. 1991.

Keeping Track of Alzheimer and Dementia Prone Patients Just Got Easier, Security Tag Systems, Inc., 1991.

Infant Monitoring System, Sekurmed.

* cited by examiner

ARTICLE LOCATING AND TRACKING SYSTEM

TECHNICAL FIELD OF THE INVENTION

This application claims priority of U.S. Patent Application Ser. No. 60/289,432, filed May 8, 2001, the disclosure of which is expressly incorporated herein by reference. The present invention is related to monitoring activities and more particularly monitoring activities of persons and equipment in a healthcare environment.

BACKGROUND AND SUMMARY OF THE INVENTION

Caregivers such as nurses and other staff in a hospital ward, hospital wing, or other healthcare facility generally work under high pressure, high stress and long hours. These caregivers should be highly responsive to patient needs, in non-emergency as well as emergency situations. Due to ever-increasing costs of healthcare and other economic practicalities, efficient deployment of the caregivers in a healthcare facility is desired, particularly at night when the number of caregivers is typically maintained at a minimum. Nevertheless, optimizing efficiency is of secondary importance relative to the primary objective of providing a high level of healthcare.

One approach to maximizing the efficiency of caregivers such as nurses in a hospital facility involves the use of a location and identification system to continuously monitor the location of the caregivers. For instance, U.S. Pat. No. 4,275,385 to White, which is incorporated herein by reference, discloses a personnel locating system where individuals to be located wear transmitters, and each transmitter transmits a signal which corresponds to the identity of the wearer. This information is relayed to and displayed at a central control unit. The information may also be displayed at remote terminals, used to control access to equipment or locations, or conveyed via a telephone interface to a telephone switching network to call the nearest telephone or to page the wearer of the transmitter. Additionally, newer communications systems provide even more than the relatively simple locating and telephoning features disclosed in White. For example, U.S. Pat. No. 5,561,412 to Novak et al.; U.S. Pat. No. 5,699,038 to Ulrich et al.; and U.S. Pat. No. 5,838,223 to Gallant et al., all of which are incorporated herein by reference, disclose the use of communications systems that integrate several aspects of personnel and equipment locating, call/code enunciation, and equipment status information.

As alluded to above, caregiver (e.g., nurse) to patient ratios continue to decline due to increasing economic pressures. Many healthcare facilities are exploring ways to reduce the non-value added activities of the caregivers (e.g., nurses) in order to maintain quality care while reducing the number of caregivers per patient. Computers hold promise for aiding the caregivers to work more efficiently by eliminating activities previously performed by caregivers and/or reducing the amount of time associated with the performance of caregiver activities. However, conventional uses of computers in the above locating and identification systems only supply the caregivers with information and at the most alarms indicating possible adverse events. Computer systems need to become aware of activities within the hospital environment if they are to reduce employee workload. To enable this evolution in computing technology, Activity Based Tracking ("ABT") is needed. ABT is, in a general sense, the real-time connectivity of information (i.e. location, time, and device activity, etc.) to detect the occurrence of a specific activity for which a known response is acted upon by an automated system.

Generally speaking an ABT system performs better if the ABT system includes a locating and detection system with a relatively high location resolution. In other words, the instances in which the ABT system provides value to the caregiver are increased if the ABT system is able to determine the location of caregivers, patients, equipment, etc. with high resolution. Current tracking/locating systems used in hospitals are based on IR/RF in which the location of the fixed receiver determines the location of the tagged object. Utilizing this strategy, to increase the locating resolution (e.g., to move from being able to determine which room a caregiver is in to being able to determine that the caregiver is next to a patient's bed), additional receivers with limited range must be employed.

Pursuant to a first embodiment of the present invention there is provided a badge for tagging objects for use with a locating and/or activity based tracking system. The locating and/or activity based tracking system includes a master station and absolute reference point sensors that are in communication with the master station. The absolute reference point sensors are configured to receive tag ID information from the badge whenever the badge passes within a predefined range of the absolute reference point sensor. The absolute reference point sensors provide the master station with the received tag ID information and information identifying the particular absolute reference point sensor that received the tag ID information. From this received information, the master station determines a reference location for the badge and the associated tagged object that corresponds to the absolute reference point sensor that received the tag ID information. The badge further includes a displacement sensor that generates signals indicative of motion and heading of the badge. The transmitter periodically transmits the motion and heading information to the master station which enables the master station to update the location of the object in relation to a previously known location for the object.

Pursuant to another embodiment of the invention there is provided an activity based tracking system that aids a caregiver in preventing an extubation of a patient. In general, a master station of the activity based tracking system uses information received from badges and equipment sensors to detect whether a patient who is using a ventilator is lying near or against a side rail of a bed. If the master station determines that a patient who is using a ventilator is lying near or against a side rail of a bed, then the master station causes a extubation prevention notification to be sent to the caregiver assigned to the identified patient.

Pursuant to another embodiment of the invention there is provided an activity based tracking system that aids a caregiver in preventing a patient from falling from bed. In general, a master station of the activity based tracking system uses information received from badges and equipment sensors to detect whether a patient is lying near or moving toward a bed side rail that is in a down position. If the master station determines that a patient is lying near or moving toward a bed side rail in the down position, then the master station causes a fall prevention notification to be sent to the caregiver assigned to care for the identified patient.

Pursuant to another embodiment of the invention there is provided an activity based tracking system that aids in gathering data for a simulation modeling tool. In general, a master station of the activity based tracking system continually receives information from badges, equipment sensors, and absolute reference position sensors. If the master station determines that the information is associated with an activity for which the master station has been preconfigured to gather data for later simulation modeling, then the master station records the received data. The master station further tracks the length of time to complete activities and the length of time tagged objects participate in the activity.

Additional features and advantages of the present invention will be evident from the following description of the drawings and exemplary embodiments.

DETAILED DESCRIPTION OF EXEMPLARY EMBODIMENTS

Figure 1:
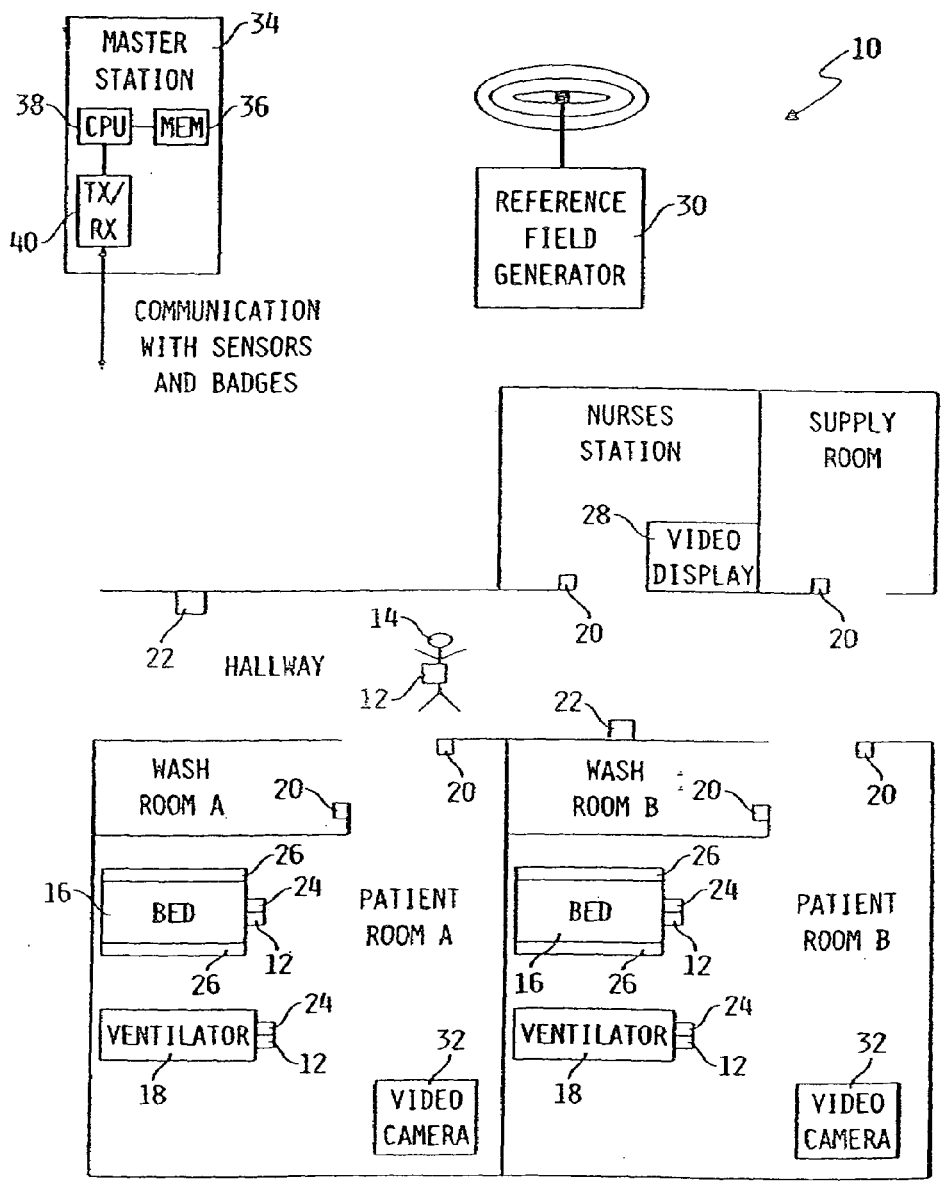
FIG. 1 illustrates an exemplary activity based tracking system that incorporates various features of the present invention.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

FIG. 1 illustrates an exemplary activity based tracking (ABT) system 10 which incorporates various features of the present invention therein. In general, the ABT system 10 is operable to monitor activities and cause execution of actions in response to various activities. The exemplary ABT system 10 includes badges 12 used to tag persons 14 and equipment such as beds 16 and ventilators 18. As further described below, badges 12 may include passive RFID, active RF, or active IR transmitters. The exemplary ABT system 10 also includes short range absolute reference position (ARP) sensors 20 operable to communicate with badges 12 and long range sensors 22 operable to communicate with badges 12. As further described below, sensors 20, 22 may include passive RFID, active RF, or active IR sensors. The exemplary ABT system 10 further includes equipment sensors 24 operable to provide use and/or status information associated with equipment such as beds 16, ventilators 18, and bed side rails 26. The exemplary ABT system 10 also includes video displays 28, an optional reference field generator 30, video cameras 32, and a master station 34.

The master station 34 is generally operable to receive information from the badges 12 and the equipment sensors 24, process the received information, and cause some action to be taken in response to determining that the received information satisfies predefined criteria or rules. The master station 34 includes memory 36, a processor 38, a transceiver 40, and software stored in the memory 36. The software when executed by the processor 38 generally causes the master station 34 to monitor persons 14 and equipment and cause certain actions to be taken in response to activities of the persons 14 and equipment. More details concerning the types of activities monitored, the manner of monitoring the activities, and the types of actions taken in response to the monitored activities are described below with reference to FIGS. 4-8.

As illustrated, the exemplary master station 34 is essentially a centralized computing system that executes software that causes the master station 34 to implement appropriate logic for activity based tracking. However, the master station 34 may alternatively be implemented in a distributed manner with multiple computing systems working together to implement the logic. In particular, the master station 34 may be implemented with a server cluster or server farm comprising several computing systems. Moreover, the master station 34 may also incorporate computational power of hospital equipment distributed throughout the facility such as beds, monitoring devices, docking stations, etc. in order to distribute portions of the computational burden associated with the logic to many processors.

The transceiver 40 of the master station 34 is coupled to the ARP sensors 20 and long range sensors 22 via a computer network or direct wiring in order to receive and/or transmit information therebetween. Moreover, the transceiver 40 of an exemplary embodiment is also coupled to some of the equipment sensors 24 via a computer network or direct wiring in order to receive and/or transmit information therebetween. Alternatively, the transceiver 40 includes wireless transmitters and receivers in order to wirelessly communicate with some or all of the ARP sensors 20, long range sensors 22, and/or the equipment sensors 24.

The optional reference field generator 30 is generally operable to provide a reference field from which the badges 12 generate heading information. As described below, the exemplary badges 12 include magnetoresistive sensors that provide signals indicative of the sensors' orientation to a reference field such as Earth's magnetic field. The reference field generator 30 is typically configured to generate a stronger magnetic field than the Earth's magnetic field. As a result, the badges 12 used with the reference field generator 30 typically include a low cost magnetoresistive sensor that does not require tilt detection or tilt correction.

Figure 9:
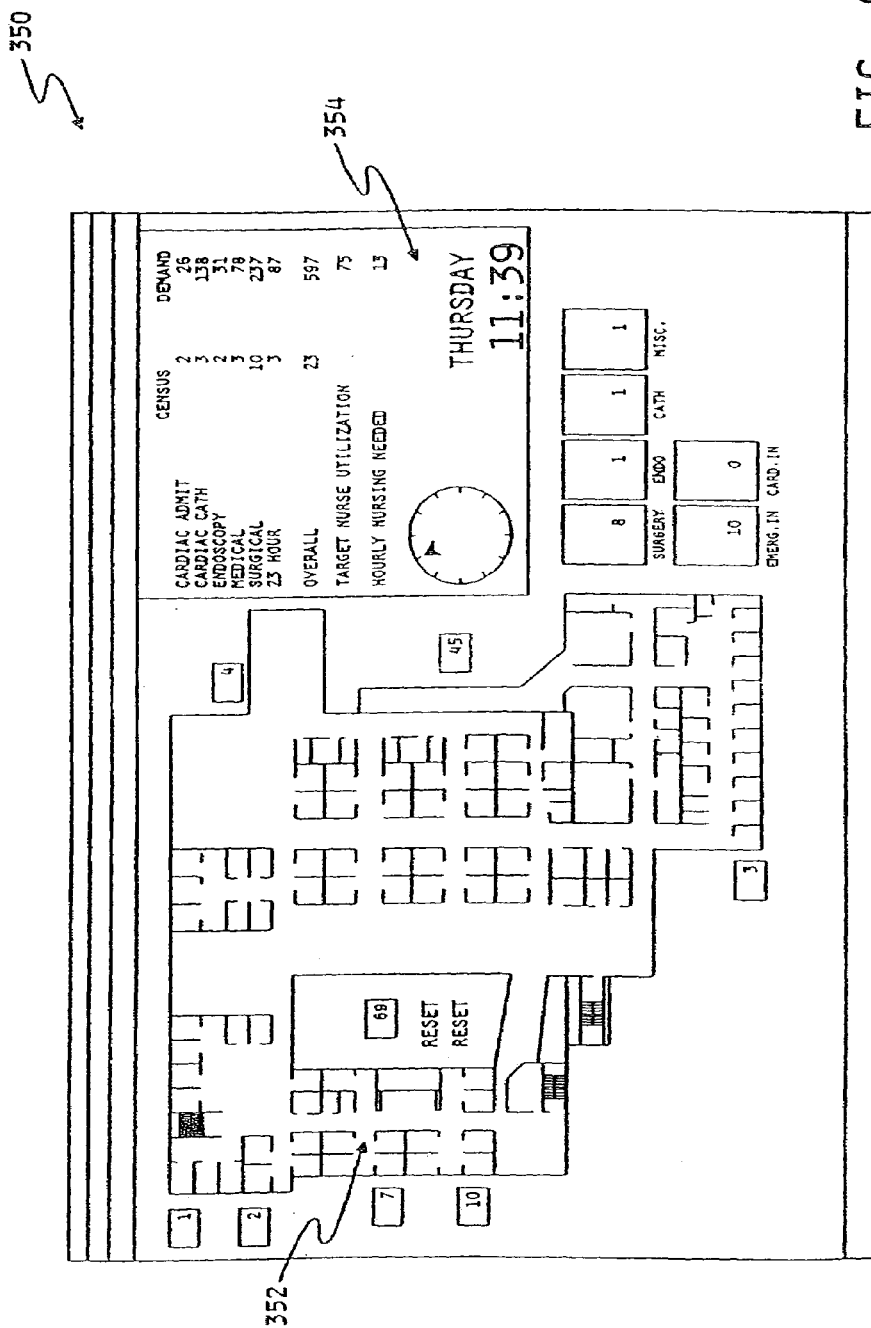
FIG. 9 illustrates an exemplary display generated by the activity based tracking system of FIG. 1.

The video displays 28 of the ABT system 10 are positioned at various locations throughout the facility (e.g., nurses' stations, hallways, utility rooms). The video displays 28 are operable to provide a graphical representation of the facility including the locations of tagged objects in the facility and the status of various equipment 15 in the facility as illustrated in FIG. 9. Moreover, in an exemplary embodiment, at least a portion of the video displays 28 are also operable to display representations of real-time streaming video. The video displays 28 are implemented using various display technologies such as televisions, computer CRTs, liquid crystal displays (LCDs), light emitting diodes (LEDs), and display panels. In an exemplary embodiment, handheld devices such as a Palm™ Pilots, or Handspring™ Visors which are carried by the caregivers also include video displays 28.

The badges 12 are generally worn by persons 14 (e.g., doctors, nurses, interns, orderlies, visitors, etc.) or attached to equipment to be monitored (e.g., beds 16, ventilators 18, IV pumps, etc). The badges 12 and the sensors 20, 22 generally each include a receiver, a transmitter, a combination transmitter and receiver, a transceiver, or other receiving or transmitting mechanisms suitable for communicating information between the badges 12 and the sensors 20, 22. In an exemplary embodiment, the badges 12 are operable to send information such as a tag ID that uniquely identifies a given badge 12 and/or displacement information indicative of motion and heading of the badge to the sensors 20, 22. Moreover, the badges 12 of the exemplary embodiment are further operable to receive information such as an acknowledgment from the sensors 20, 22.

The sensors 20, 22 of the exemplary ABT system 10 generally include a receiver operable to receive information transmitted by badges 12. The sensors 20, 22 are also generally operable to forward the information received to the master station 34 and/or provide the master station 34 with a sensor ID that uniquely identifies the sensor 20, 22. The sensor ID enables the master station 34 to track the location of each tagged object (i.e., person 14 or equipment) based upon which sensors 20, 22 received information from the badges 12 of tagged objects as the tagged objects move through the facility.

According to one embodiment of the invention, a person 14 may enter a floor of a hospital wearing a badge 12. The system recognizes that person 14 has entered the floor when person 14 moves within range of ARP sensor 20, whereupon the passive RFID of badge 12 was activated and transmitted an ID associated with badge 12 (and person 14). The ID was received by an sensor 20 including an RFID integrator located at a doorway entrance to the floor. As further explained herein, the network establishes an initial location point for person 14 by knowing the specific location of the RFID integrator. The RFID integrator may also be configured to transmit, for example, patient assignments to person 14, which are received by badge 12 and stored in badge memory 36. The system may then detect person 14 in a hallway of the floor with a sensor 22 including an active RF sensor for detecting ID signals transmitted by badge 12 with an active RF transmitter that periodically transmits the ID signal (e.g., every 5 seconds). As person 14 enters a patient room, the system may detect three signals from person 14 (i.e., an active RF signal indicating that person 14 is on the floor, an active IR signal indicating that person 14 is in a specific patient room, and a passive RFID signal indicating that person 14 is in the door entryway to the specific patient room. By installing RFID integrators at different locations within such patient rooms, the system may accomplish increased resolution regarding the location of person 14 within the room.

In an exemplary embodiment, each badge 12 includes a passive RF transmitter which is fully or partially powered by an ARP sensor 20 when in close proximity with the ARP sensor 20 (e.g., within 3 feet). In response to being in close proximity to the ARP sensor 20, the passive RF transmitter of the exemplary badges 12 transmits the identification signal to the ARP sensors 20. For example, the RF transmitter of a badge 12 transmits the identification signal to an RF receiver of an ARP sensor 20 in the doorway of patient room A when the badge 12 passes through the doorway of the patient room A. The ARP sensor 20 then provides information identifying the particular badge 12 to the master station 34 and information identifying the particular ARP sensor 20 for further processing and recording. In an exemplary embodiment, the ARP sensor 20 includes an RF identification receiver or a limited focus IR receiver. In general, the ARP sensor 20 enables the master station 34 to establish a very specific location of a badge 12. More specifically, the ARP sensors 20 are used by the master station 34 to re-calibrate the location of the badges 12 as they pass within close proximity of the ARP sensors 20.

In one embodiment of the ABT system 10, visitors and patients are also provided with badges 12 to enable the master station 34 to monitor their movements through the facility. In such an embodiment, visitors and patients are given active badges which actively transmit an identification signal. In an alternative embodiment, visitors and patients are given passive badges which transmit an identification signal when in close proximity to one of the ARP sensors 20 located throughout the facility.

The badges 12 may also be attached to equipment (e.g., IV pumps, beds 16, ventilators 18, carts, diagnostic equipment, or the like) to be monitored by the ABT system 10 and generally enable the location of equipment to be tracked throughout the facility. As a result of providing the ABT system 10 with information concerning the location of equipment, the ABT system 10 causes actions to be executed based upon the location of the equipment and/or persons' interactions with such equipment.

The equipment sensors 24 are generally associated with equipment and generally enable the ABT system 10 to monitor the use and/or status of such equipment. For example, equipment sensors 24 are attached to the electrical plugs of the equipment to determine whether the equipment is drawing a current. In an exemplary embodiment, the badges 12 that are attached to certain equipment further include equipment sensors 24. The equipment sensors 24 enable the ABT system 10 to cause actions to be executed based upon use and/or status of the equipment. Furthermore, by reporting when the equipment is activated and deactivated, the equipment sensors 24 enable the hospital to charge patients for the actual amount of time the equipment was used instead of utilizing national averages based on the type of illness of the patient.

In an exemplary embodiment, the badges 12 and the sensors 20, 22 further include anti-collision technology that allows for information to be transferred between a single sensor 20, 22 and multiple badges 12 in a simultaneous or pseudo-simultaneous (e.g., TDMA, CDMA) manner. Use of anti-collision technology allows for several badges 12 to be detected at the same time by the same sensor 20, 22 thereby providing the ABT system 10 with the ability to identify persons 14 and equipment in close proximity to one another and accurately track their respective locations and activities.

Additional details concerning the structure and function of a suitable system for locating and tracking persons 14 and to support various other features of the present invention are disclosed in U.S. Pat. No. 5,561,412, the disclosure of which is hereby incorporated by reference. Other location and tracking systems are disclosed in U.S. Pat. No. 6,344,794 filed Jan. 7, 2000 and co-pending U.S. patent application Ser. No. 09/699,796, filed Oct. 30, 2000, the disclosures of which are hereby incorporated by reference. Additional location and tracking systems are disclosed in U.S. Pat. Nos. 4,275,385; 4,601,064; Re 35,035; 5,633,742; 5,745,272; 5,818,617; 5,119,104; 5,387,993; 5,548,637; 5,572,195;

5,291,399; 5,455,851; 5,465,082; 5,515,426; 5,594,786; 5,689,229; 5,822,418; 5,822,544; 5,699,038 and 5,838,223.

In an exemplary embodiment, the badges 12 are implemented in a manner similar to the badges described in U.S. Pat. No. 5,561,412, U.S. Pat. No. 6,344,794, and co-pending U.S. patent application Ser. No. 09/699,796 in which the location of a badge 12 is determined solely upon which sensors of the location and tracking system detect the badge 12.

Figure 2:
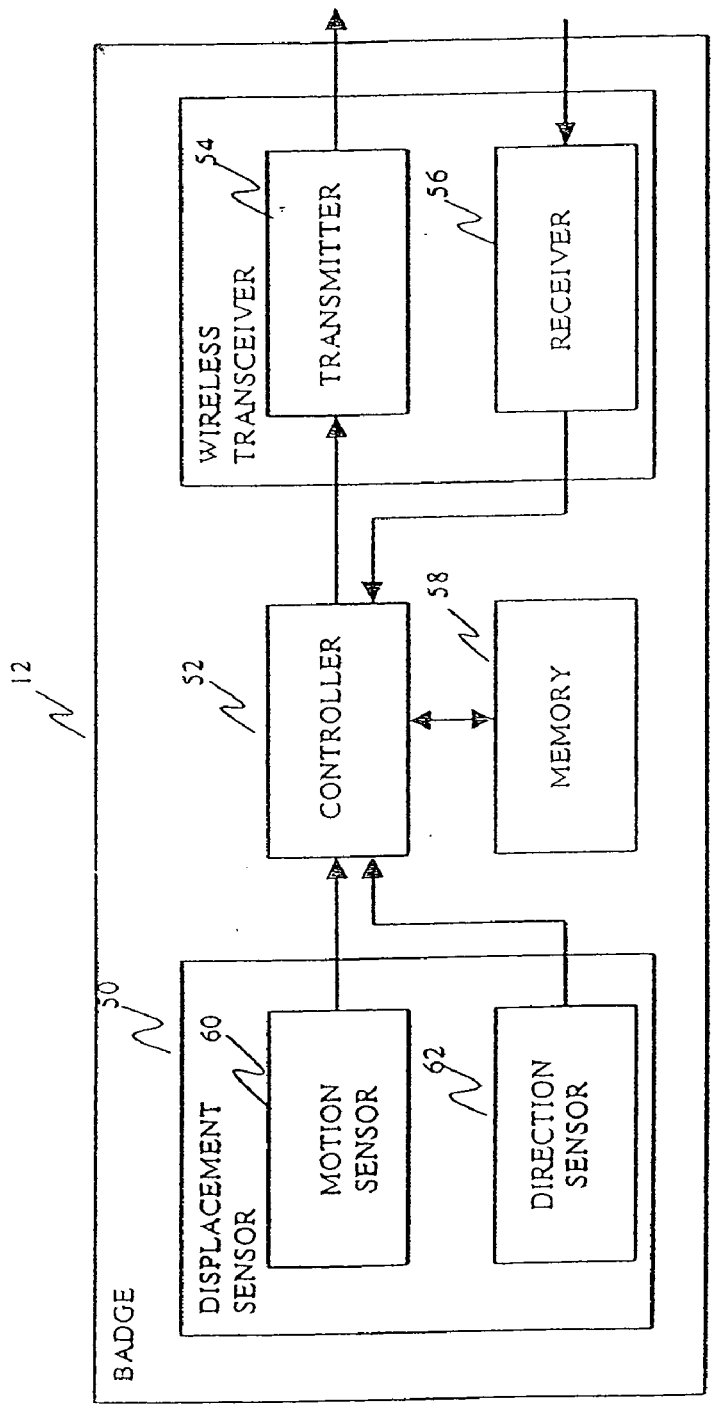
FIG. 2 illustrates an exemplary badge of the activity based tracking system shown in FIG. 1.

Alternatively, the badges 12 include components which aid in tracking the location of the badges 12 and thus enable a reduction in the number of sensors required to track the location the badges 12 in a fine grain manner. As depicted in FIG. 2, the exemplary badges 12 include a displacement sensor 50, a controller 52, a transmitter 54, a receiver 56, and a memory 58. The displacement sensor 50 is configured to generate one or more signals the combination of which is indicative of a motion and a heading of a "tagged object." As indicated above, tagged objects include persons (e.g., doctors, nurses, orderlies, visitors, etc.), and equipment (e.g., a hospital bed 16, IV pumps, ventilators 18, heart monitors, medication containers, charts, portable televisions, etc.), or any other tangible thing desired to be located and/or tracked.

As depicted, the displacement sensor 50 generally comprises a motion sensor 60 and a direction sensor 62. The motion sensor 60 is generally operable to sense movement of the tagged object and generate one or more signals that in combination are indicative of the sensed movement. The motion sensor 60 includes a mono-axis, dual-axis, or tri-axis accelerometer which generates one or more signals that in combination are indicative of the dynamic acceleration (e.g., vibration induced acceleration) and/or static acceleration (e.g., gravity induced acceleration) of the tagged object. In particular, the motion sensor 60 of the exemplary embodiment includes an ADXL202 accelerometer from Analog Devices which is a low cost, low power, complete 2-axis accelerometer with a measurement range of ±2 g. The ADXL202 accelerometer measures both dynamic acceleration (e.g., vibration) and static acceleration (e.g., gravity) and generates a first Duty Cycle Modulated ("DCM") signal whose duty cycle (ratio of pulsewidth to period) is proportional to the acceleration in a first sensitive axis (e.g., x-axis) and a second DCM signal whose duty cycle is proportional to acceleration in a second sensitive axis (e.g., y-axis).

The following Analog Devices publications further describe the ADXL202 accelerometer and methods for relating the sensed accelerations to distances traveled: "ADXL202/ADXL201—Low cost ±2 g/±10 g Dual Axis iMEMS® Accelerometers with Digital Output" (Datasheet, Rev. B—4/99) and "Using the ADXL202 in Pedometer and Personal Navigation Applications," by Harvey Weinberg, the disclosures of which are hereby incorporated herein by reference.

The direction sensor 62 of the displacement sensor 50 is generally operable to generate one or more signals that in combination are indicative of the directional orientation or heading of the badge 12 with respect to a reference direction and therefore indicative of the direction traveled by the object tagged with the badge 12. The direction sensor 62 of the exemplary embodiment includes a two-dimensional magnetoresistive field sensor such as the Philips KMZ52 sensor or two one-dimensional magnetoresistive field sensors such as the Philips KMZ51 which generate one or more signals indicative of the horizontal orientation of the badge 12 with respect to a reference direction such as magnetic north, true north, or some other direction defined by an associated reference field such as the Earth's magnetic field or an artificially generated field such as that generated by reference field generator 30. The exemplary direction sensor 38 further includes support electronics such as a flip coil driver and pre-amps which are used to calibrate the field sensors and interface the field sensors with the controller 32 as explained in Philips Semiconductor publication "Electronic Compass Design using KMZ51 and KMZ52", Application Note AN00022, dated Mar. 30, 2000.

As indicated above, the exemplary ABT system 10 includes a reference field generator 30 that enables the badge 12 to be implemented without tilt correction. However, in an alternative exemplary embodiment, the direction sensor 62 further includes mechanical or electrical gimbaling components that maintain the two sensitive axes of the field sensor in a horizontal plane (e.g., maintain an x-axis and a y-axis perpendicular with Earth's gravity). To support electronic gimbaling or tilt compensation, the direction sensor 62 includes a three-dimensional field sensor and a pitch-and-roll sensor. The three-dimensional field sensor includes three sensitive orthogonal axis sensors that generate one or more signals which in combination are indicative of a three-dimensional spatial orientation of the badge 12 with respect to a reference field such as Earth's magnetic field or a generated field such as that generated by the reference field generator 30. Further, the pitch-and-roll sensor generates one or more signals indicative of the orientation of the field sensor with respect to gravity. In particular, the pitch-and-roll sensor includes a two-dimensional accelerometer, such as the ADXL202 accelerometer described above, including two orthogonal axis sensors that generate one or more signals. These signals, in combination, are indicative of the static acceleration experienced by the badges 12 due to gravity.

The transmitter 54 of the badges 12 is coupled to the controller 32 to receive one or more signals indicative of information to be transmitted. Similarly, the receiver 56 is coupled to the controller 52 to provide the controller 52 with one or more signals indicative of information received. The transmitter 54 and the receiver 32 include infrared (IR), radio frequency (RF), and/or other wireless transmission and reception components which utilize one or more different transmission protocols. More specifically, as indicated above, the transmitter 52 includes a passive RF transmitter to transmit identification information such as a tag ID to the ARP sensors 20. Passive RF transmitters i) do not require battery power to transmit information, and ii) generally must pass close to an ARP sensor 20 in order to transmit information which insures a high resolution point for the absolute position.

The controller 52 in general controls the transmission and reception of information to and from the badges 12. In an exemplary embodiment, the controller 52 is implemented with a low cost microcontroller such as the MicroChip PIC16C54. Besides controlling the transmission and reception of information to and from the badges 12, the controller 52 also processes the displacement signals received from the displacement sensor 50 and stores displacement samples in the memory 58 that are representative of the motion and heading of the badges 12 as sensed by the displacement sensor 50. In particular, the controller 52 in an exemplary embodiment processes one or more motion signals from the displacement sensor 50 to obtain motion data that is indicative of the speed of the badge 12 and heading data indicative of the heading of the badges 12.

Figure 3:
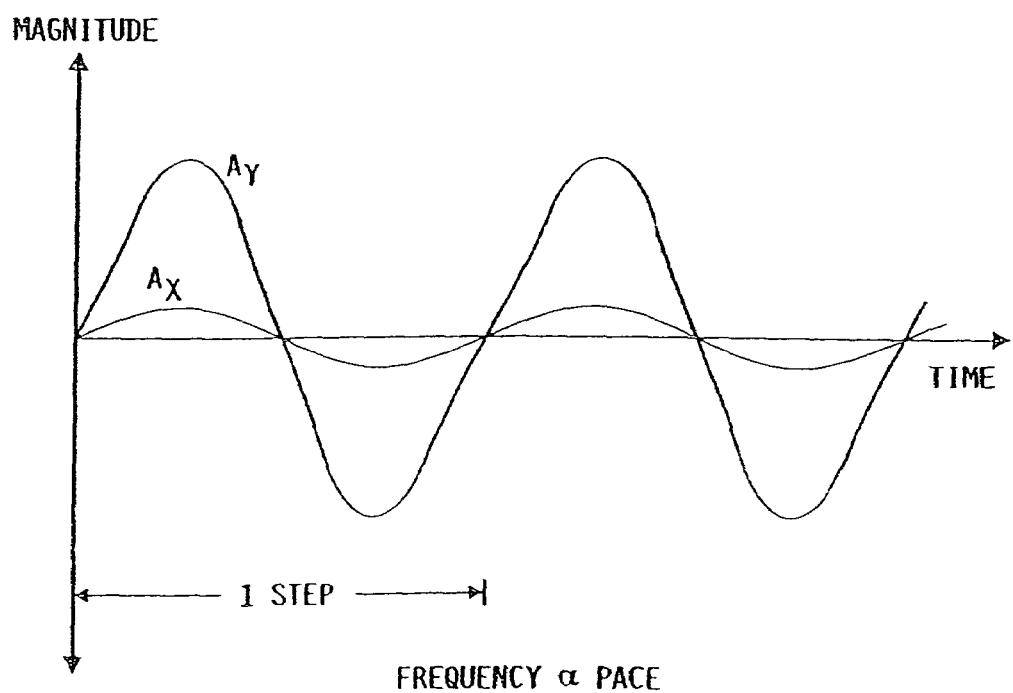
FIG. 3 illustrates typical movement of the badge shown in FIG. 2 when a object tagged with the badge is in transit.

FIG. 3 shows waveforms representing an exemplary vertical acceleration, "$A_y$," and an exemplary horizontal acceleration, "$A_x$," of a person walking or running. In general, pedestrian travel is fairly rhythmic pursuant to the gait of the pedestrian. Accordingly, as the person walks or runs through the facility, the badge 12 attached to the person is accelerated vertically and horizontally in generally periodic fashions. Each step or stride taken by the person is detectable as the period of $A_y$. Thus, the frequency of $A_y$ is proportional to the number of steps taken by the caregiver per unit of time, which is proportional to the approximate pace at which the person walks or runs.

In the exemplary embodiment discussed above in connection with FIG. 2, the controller 52 receives one or more signals from the displacement sensor 50 that are indicative of the vertical acceleration $A_y$. In the exemplary embodiment, the controller 52 determines the approximate speed of movement of the person by processing the received signals to obtain the frequency of the vertical acceleration $A_y$ which is indicative of the speed of the person.

In the case of a wheeled objects or an object on skids (e.g., hospital beds 16, carts, tables, etc.) the accelerations imparted to the tag or badge 12 attached to the object are fairly periodic in nature due to each revolution of the wheel(s) or vibrations of the skid(s). In an exemplary embodiment, a ridge or a bump is added to a wheel of a wheeled object in order to aid in the generation of a discernable amount of acceleration. In any event, although the relationship of the vertical acceleration $A_y$, horizontal acceleration $A_x$, and time may vary between different types of assets, and even between different pedestrians, the fairly periodic nature of the accelerations imparted to the badges 12 while the object is in motion are readily discernable via the appropriate signal processing algorithms. Moreover, the displacement sensor 50 may generate the signals based on other parameters that vary with the speed of movement of the object. For example, the displacement sensor 50 for wheeled assets may include a more conventional type speedometer that senses the rotation of the wheels and generates signals based upon the sensed rotation of the wheels.

In an exemplary embodiment, the master station 34 receives the displacement samples from the badges 12 and further processes the displacement samples to obtain an estimated distance traveled and an estimated heading traveled. In particular, the master station 34 determines the estimated distance traveled based upon the motion data received from the badges 12 in a manner similar to one of the methods described in "Using the ADXL202 in Pedometer and Personal Navigation Applications," by Harvey Weinberg. The master station 34 also determines an estimated heading traveled from the motion data and/or the heading data received from the badges 12. In particular, the master station 34 performs one or more of the following functions on the motion data and/or the heading data: offset-elimination, temperature drift compensation, non-orthogonality correction of sensor axes, interference field correction, declination compensation, tilt compensation, and true north compensation in a manner similar to those described in "Electronic Compass Design Using KMZ51 and KMZ52." Alternatively, the controller 52 of the badges 12 may be implemented with a more powerful processor which executes software or firmware instructions to implement all or portions of the functions performed on motion data and/or heading data described above.

Figure 4:
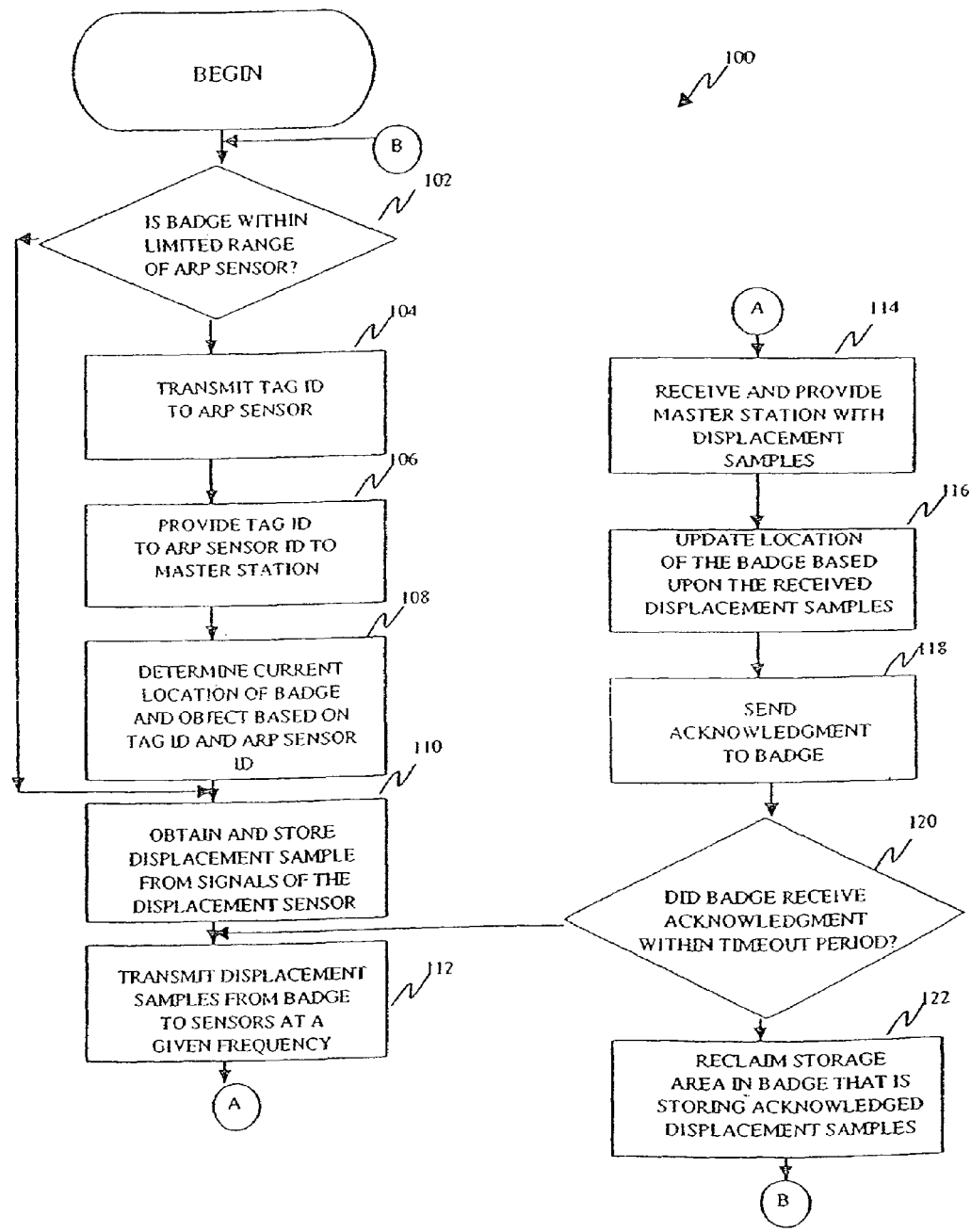
FIG. 4 illustrates an exemplary location method used by the activity based tracking system of FIG. 1 to determine the location of tagged objects based upon information received from the badges of the tagged objects.

Shown in FIG. 4 is a location tracking method 100 used to track the location of objects tagged with badges 12. In step 102, the badge 12 determines whether the badge 12 is within the limited range of an ARP sensor 20. If the badge 12 is within range of the ARP sensor 20, then the badge 12 in step 104 transmits a tag ID to the ARP sensor 20 that uniquely identifies the badge 12. More specifically, the badge 12 includes a passive RF transmitter that is powered by the ARP sensors 20 when in range of the ARP sensors 20. Accordingly, the badge 12 determines that the badge 12 is within range of the ARP sensor 20 if the transmitter 54 of the badge 12 is powered by the ARP sensor 20. In step 104, the ARP sensor 20 that receives the information from the badge 12 provides the master station 34 with the tag ID received from the badge 12 and a sensor ID that identifies the ARP sensor 20.

In a power saving embodiment of the badge 12, the ARP sensor 20 in step 104 further causes the badge 12 to power active portions of the badge 12 (e.g., displacement sensor 50, controller 52) with an on-board battery (not shown). In particular, after receiving power from the ARP sensor 20 and initiating battery operation of the active portions, the badge 12 continues to power the active portions until the controller 52 detects a power off condition. For example, the controller 52 may remove battery power from the active portions of the badge 12 after determining that the badge 12 has not received transmissions from the sensors 20, 22 for a predetermined time period (e.g., 10 minutes), and/or that the badge 12 has been static (i.e., substantially still) for a predetermined time period (e.g., 5 minutes).

In step 106, the master station 34 determines the location of the badge 12 and associated tagged object from the tag ID and the sensor ID. More specifically, the master station 34 includes facility map information that defines the location of doorways, walls, ARP sensors 20, and other static features of the facility. From the facility map information and the information received from the ARP sensor 20 in step 104, the master station 34 determines that the current location of the tagged object is the ARP sensor 20 identified by the received sensor ID.

The badge 12 in step 108 starts transmitting displacement samples at a predetermined interval (e.g., every 5 seconds). In an exemplary embodiment, the badge 12 transmits signals representative of the tag ID and all displacement samples that have been stored in the memory 58 since receiving an acknowledgment of a prior displacement sample transmission. In an exemplary embodiment, the controller 52 obtains displacement samples from the displacement signals of the displacement sensor 50 on a predetermined interval (e.g., 1 millisecond intervals) and stores the obtained displacement samples in the memory 58. In particular, the controller 52 periodically samples the received displacement signals during the given interval to obtain displacement samples that are generally representative of the displacement signals during the interval. After obtaining the displacement samples for the interval, the controller 52 stores the displacement samples in the memory 58. In an alternative embodiment, the badge 12 transmits the displacement samples at various different intervals depending upon the rate of movement of the badge 12 as described in U.S. Patent Application 60/306,818, filed Jul. 20, 2001, and entitled "Locating Badge with Intelligent Transmission Based on Acceleration," the disclosure of which is hereby incorporated by reference.

In an alternative embodiment, the controller 52 combines displacement samples in order to reduce the number of displacement samples stored in the memory 58. In particular, the controller 52 combines displacement samples that are temporally adjacent to one another and that do not significantly differ from one another. For example, if the controller 52 determines that the motion and heading of temporally adjacent displacement samples are within a predetermined tolerance, then the controller 52 combines the two displacement samples (e.g., averaging the samples, discarding one of the samples) to obtain a displacement sample representative of the interval associated with both displacement samples. In this manner, the controller 52 obtains a single displacement sample that is representative of several temporally adjacent displacement samples thus reducing the number of samples stored in the memory 58.

Further, the controller 52 of the alternative embodiment includes timing information with the displacement samples. For example, the controller 52 includes a count value with the motion data and heading data of the displacement samples to indicate the number of samples of which the stored displacement sample is representative. Alternatively, the controller 52 includes a timestamp value with the displacement samples. The controller 52 may instead utilize other techniques for correlating the motion data and heading data of a displacement sample to a respective time interval such as including an interval sequence count with the displacement samples.

As a result of periodically transmitting the displacement samples and tag ID in step 112, receivers of the sensors 22 in step 114 receive signals that are representative of the displacement samples and tag ID of the badge 12. The sensors 22 further provide the master station 34 with information representative of the tag ID and displacement samples in step 114.

The master station 34 in step 116 determines the movement path and location of the badge 12 based upon the received tag ID, displacement samples, and the previously determined location for the badge 12 (e.g., location of an ARP sensor 20, or location determined from displacement samples). The master station 34 processes the motion data, heading data, and optionally the timing data of the displacement samples to determine the movement path of the badge 12. Techniques for obtaining distance information from motion data are described in the previously referenced Analog Devices publications.

The master station 34 in step 116 further adjusts the movement path and location to prevent a conflict between the calculated movement path for the badges 12 and the layout information for the facility. For example, the calculated movement path may indicate that the tagged object passed through a wall at a location near a doorway and then proceeded down a hallway outside the doorway. The master station 34 may alter the calculated movement path to indicated that the tagged object passed through the doorway which is the more likely scenario. Methods such as fuzzy logic, neural networks, expert systems, and/or other artificial intelligence techniques for correlating location information with map information are known.

In response to receiving the tag ID and displacement samples from the badges 12, the master station 34 in step 118 causes an acknowledgment to be sent to the badge 12 via a transmitter such as the RF and/or IR transmitters of the ARP sensors 20 or the long range sensors 22. If the badge 12 receives the acknowledgment, then the controller 52 in step 120 reclaims the storage area of the memory 58 used to store the acknowledged displacement samples. However, if the controller 52 determines in step 120 that the badge 12 did not receive the acknowledgment message within a predefined timeout period (e.g., 1 second), then the controller 52 returns to step 112 in order to retransmit the tag ID and displacement samples.

Figure 5:
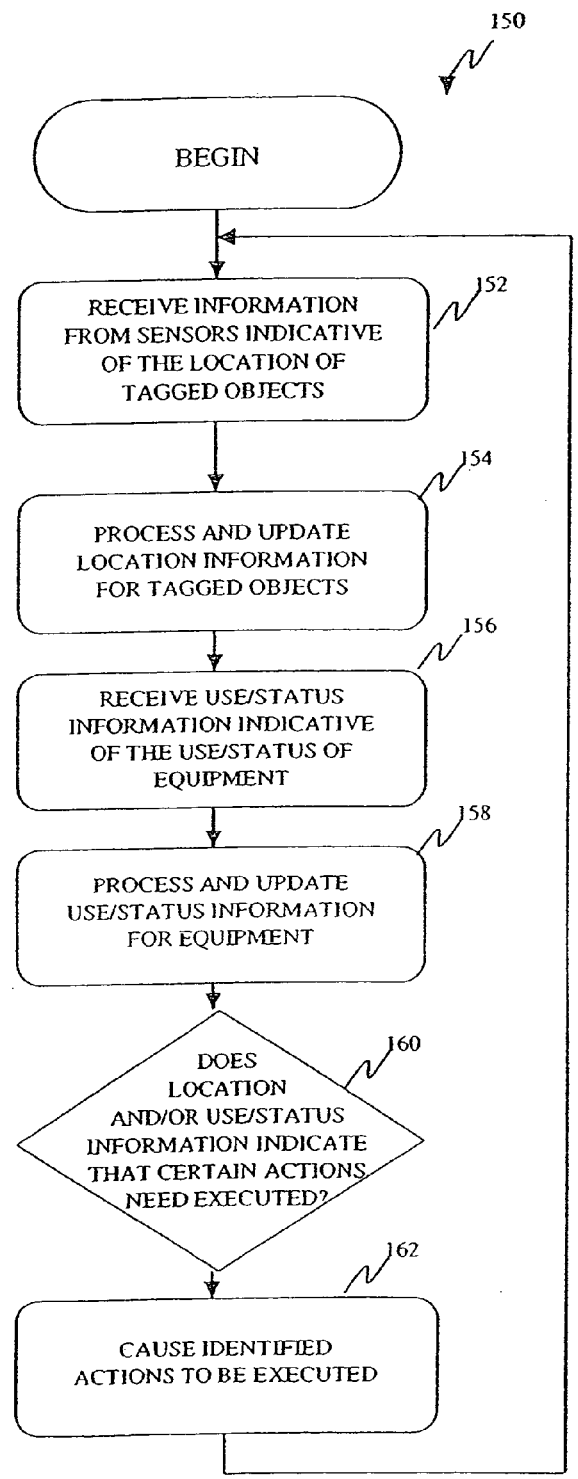
FIG. 5 illustrates an exemplary activity based tracking method used by the activity based tracking system of FIG. 1 to perform activity based tracking.

Referring now to FIG. 5, there is depicted an activity based tracking method 150 implemented by the ABT system 10. The master station 34 of the ABT system 10 in step 152 receives information from the ARP sensors 20 that is indicative of the location of tagged objects associated with the badges 12. The master station 34 in step 154 processes the information received in step 152 and updates location information for the tagged objects associated with the badges 12 accordingly.

The master station 34 also receives in step 156 information from the equipment sensors 24 that is indicative of the use/status of the equipment associated with the equipment sensors 24. In step 158, the master station 34 processes the information received in step 156 and updates use/status information for the equipment associated with the equipment sensors 24.

The master station 34 in step 160 analyzes the updated location and use/status information to determine whether actions need to be taken in response to the received information. In particular, the master station 34 determines for each predefined rule whether all conditions associated with the rule have been satisfied. If the updated location and/or use/status information satisfies the conditions of a given rule, then the master station 34 in step 162 causes actions associated with each satisfied rule to be executed. However, if the master station 34 determines that no predefined rule has been satisfied, then the master station 34 returns to step 62 in order to process additional information from the ARP sensors 20 and the equipment sensors 24.

Hygiene monitoring systems that monitor handwashing and equipment washing are disclosed in copending U.S. patent application Ser. No. 09/699,796, filed Oct. 30, 2000 and are exemplary embodiments of the activity based tracking method 100. In particular, the hygiene monitoring systems receive information indicative of the location of caregivers and handwashing devices and use/status information indicative of the use of the handwashing devices. From this information, the hygiene monitoring systems determine whether a caregiver needs to wash their hands to maintain compliance with an established hygiene policy. The disclosure of U.S. patent application Ser. No. 09/699,796, filed Oct. 30, 2000 and entitled "Hygiene Monitoring System" is hereby incorporated by reference.

Figure 6:
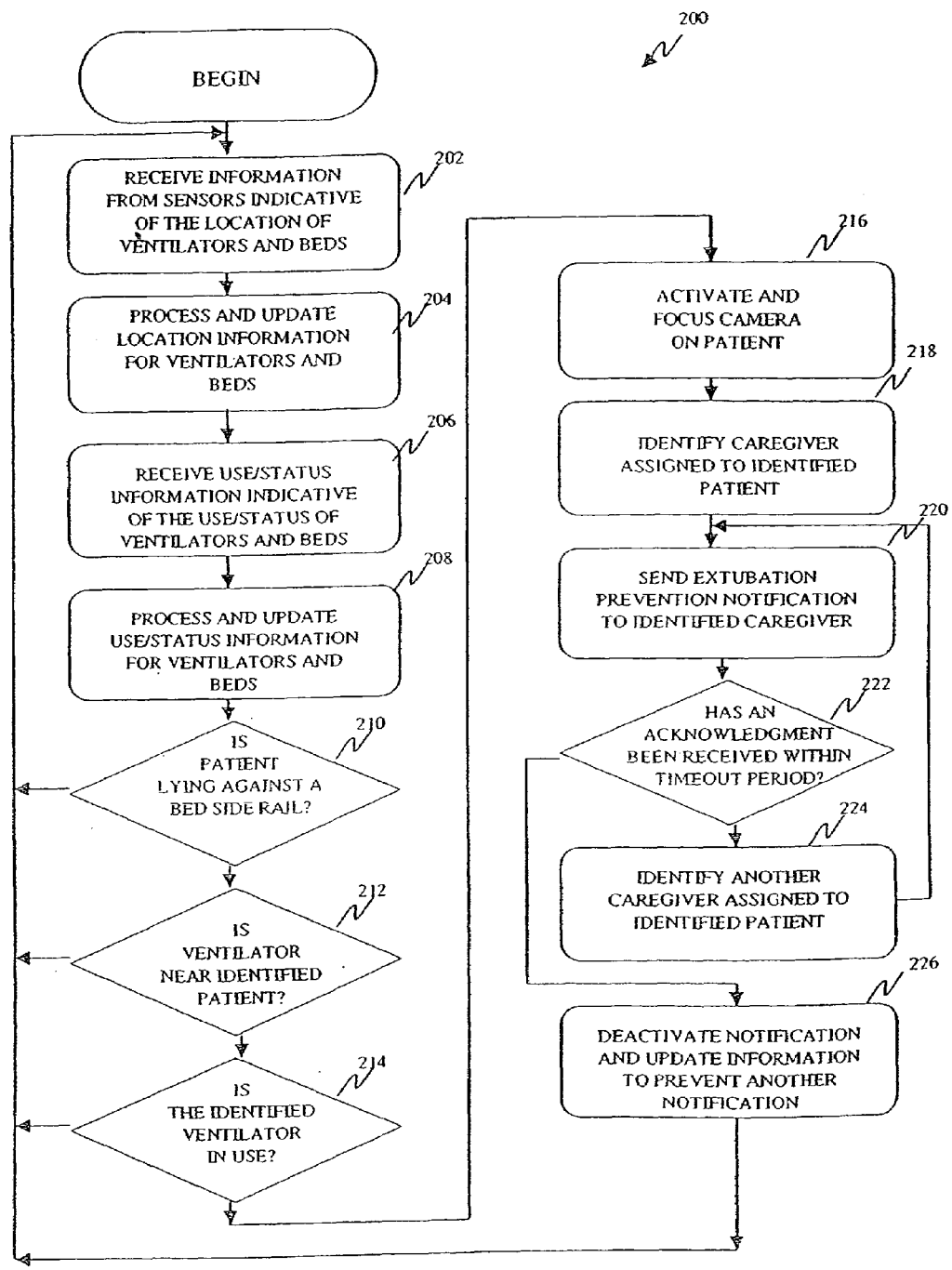
FIG. 6 illustrates an exemplary extubation prevention method which is a particular embodiment of the activity based tracking method shown in FIG. 5.

Referring now to FIG. 6, there is depicted an exemplary extubation prevention method 200 which is a particular embodiment of the ABT method 150. Experience has shown that extubation is more likely if a patient is lying against a side rail 26 of a bed 16 while on a ventilator 18. Extubation may result in harm to the patient and lost work time to re-establish the breathing pathway. When executing the extubation prevention method 200 of FIG. 6, the ABT system 10 generally determines whether a patient is using a ventilator 18 while lying against a side rail 26 of a bed 16. If the patient is using a ventilator 18 while lying against a bed side rail 26, then the ABT system 10 alerts a caregiver via a pocket pager or badge 12 and may provide the caregiver with streaming video of the patient via a pocket pager, badge 12 or a nearby video display 28. With such information, the caregiver determines whether corrective action is needed in order to prevent a possible extubation.

The master station 34 in step 202 receives location information from badges 12 of tagged beds 16 and badges 12 of tagged ventilators 18 that is indicative of the location of the tagged beds 16 and tagged ventilators 18. The master station 34 in step 204 processes the location information received in step 202 and updates location information for the tagged beds 16 and ventilators 18.

The master station 34 of the ABT system 10 in step 206 receives use/status information from equipment sensors 24 of beds 16 and ventilators 18 that is indicative of the use and/or status of the beds 16 and ventilators 18. More specifically, the ABT system 10 in step 206 receives use/status information from equipment sensors 24 of beds 16 that is indicative of position of patients within beds 16. In an exemplary embodiment, the beds 16 are equipped with one or more equipment sensors 24 in the bed side rails 26 that detect weight of the patient lying against the bed side rail 26. In an alternative embodiment, the beds 16 include a patient support surface having one more equipment sensors 24 that detect position of the patient upon the patient support surface as disclosed in U.S. Pat. No. 6,208,250, entitled "Patient Position Detection Apparatus for a Bed 16," the disclosure of which is hereby incorporated by reference.

The master station 34 in step 206 also receives use/status information from equipment sensors 24 of ventilators 18 that is indicative of the usage of the ventilators 18. In an exemplary embodiment, the ventilators 18 include one or more equipment sensors 24 that detect whether the ventilator 18 is in use. For example, the ventilators 18 include a current sensor, voltage sensor, and/or power sensor which respectively detect the presence or absence of an operating current, operating voltage, and/or operating power and provide the result of such detection to the master station 34. Numerous other manners for detecting whether a device such as a ventilator 18 is operating are well known in the art and any may be used with the present invention.

The master station 34 in step 208 processes the use/status information received in step 206 and updates use/status information for the beds 16 and the ventilators 18 accordingly. More specifically, the master station in step 208 updates use/status information to indicate the current position of patients in beds 16 and which ventilators 18 of the ABT system 10 are presently being used.

The master station 34 analyzes the updated location and use/status information to determine whether a patient has an increased likelihood of extubation. More specifically, the master station 34 in step 210 determines whether a patient is lying against a bed side rail 26 based upon the use/status information associated with the beds 16. If the master station 34 determines that a patient is not lying against a bed side rail 26, then the master station 34 returns to step 202 in order to process further information received from the badges 12 and the equipment sensors 24.

If the master station 34 determines that the patient is lying against a bed side rail 26, then the master station 34 further determines whether the patient is using a ventilator 18. In particular, the master station 34 determines whether a ventilator 18 is near the patient lying against the bed side rail 26 based upon location information associated with the ventilators 18. In an exemplary embodiment, the master station 34 determines that the ventilator 18 is near the patient if the location information associated with the ventilator 18 indicates that the ventilator 18 is in the same room as the patient lying against the bed side rail 26. Alternatively, the master station 34 may determine that the ventilator 18 is near the patient if the location information indicates that the ventilator 18 is within a predetermined range (e.g., 3 feet) of the patient or the bed 16 on which the patient is lying.

If the master station 34 determines that a ventilator 18 is not near the patient lying against the bed side rail 26, then the master station 34 returns to step 202 in order to process further information received from the badges 12 and the equipment sensors 24. However, if the master station 34 determines that a ventilator 18 is near the patient lying against the bed side rail 26, then the master station 34 in step 214 determines whether the ventilator 18 near the identified patient is in use based upon the use/status information associated with the ventilator 18.

If the master station 34 determines that the ventilator 18 is not in use, then the master station 34 returns to step 202 in order to process further information received from the badges 12 and the equipment sensors 24. However, if the master station 34 determines that the ventilator 18 is in use, then the master station 34 causes actions associated with preventing extubation of the identified intubated patient lying against the bed side rail 26. In an exemplary embodiment, the master station 34 in step 216 activates a camera 32 located in the room of the identified patient and focuses the camera 32 on the patient if not already focused on the patient. The master station 34 in step 218 identifies which caregiver is assigned to the identified patient based upon patient assignment data that the master station 34 either maintains or has access to.

The master station 34 in step 220 sends an extubation prevention notification to the caregiver assigned to the intubated patient lying against the bed side rail 26. More specifically, the master station 34 causes the badge 12 of the identified caregiver to provide a tactile indiction (e.g., vibrate), an audible indiction (e.g., beep), a visual indiction (e.g., blinking LED), and/or some other indication of the possible extubation situation. Furthermore, the master station 34 provides the identified caregiver with streaming video of the patient via a hospital network system such as the system disclosed in U.S. Pat. Nos. 5,561,412, 5,699,038, and 5,838,223, the disclosures of which are hereby incorporated by reference. The streaming video enables the caregiver to assess the patient specific situation to determine without physically entering the room of the patient if intervention is required. If the streaming video indicates that intervention is not required, then the caregiver is saved a trip to the patient's room thus providing a savings of time. In an exemplary embodiment, the master station 34 causes the video stream be sent to a video display 28 located near the caregiver (such as a nurse's station, hall monitor, etc.) or to a portable pager or badge 12 carried by the caregiver which has video playback capabilities.

The master station 34 in step 222 determines whether an acknowledgment was received from the caregiver within a predetermined time span (e.g., 30 seconds). The ABT system 10 provides various manners for the caregiver to acknowledge the extubation prevention notification. For example, the ABT system 10 enables the caregiver to provide the acknowledgment by actuating a mechanism (e.g., switch, button) on their badges 12, or actuating a nearby acknowledgment mechanism (e.g., switch, button) located in various locations throughout the facility such as in the patient rooms, hallways, nurses station, rest rooms, utility rooms, etc. Alternatively, the ABT system 10 enables the caregiver to provide the acknowledgment via a remote control carried by the caregiver such as the remote control disclosed in U.S. patent application Ser. No. 09/848,941, entitled "Remote Control for Hospital Bed," filed May 4, 2001, the disclosure of which is hereby incorporated by reference.

If the master station 34 determines that an acknowledgment was not received from the caregiver within the predetermined timeout period, then the master station 34 in step 224 identifies another caregiver assigned to the patient. The master station 34 then returns to step 220 in order to send an extubation prevention notification and accompanying video stream to the newly identified caregiver. However, if the maser station 34 determines that an acknowledgment was received from the caregiver within the predetermined timeout period, then the master station 34 in step 226 deactivates the extubation prevention notification and updates use/status information associated with the patient and/or the ventilator 18 such that another extubation prevention notification is not generated for the same patient for a predetermined time span (e.g., 5 minutes). The master station 34 then returns to step 202 in order to process further information received from the badges 12 and the equipment sensors 24.

Figure 7:
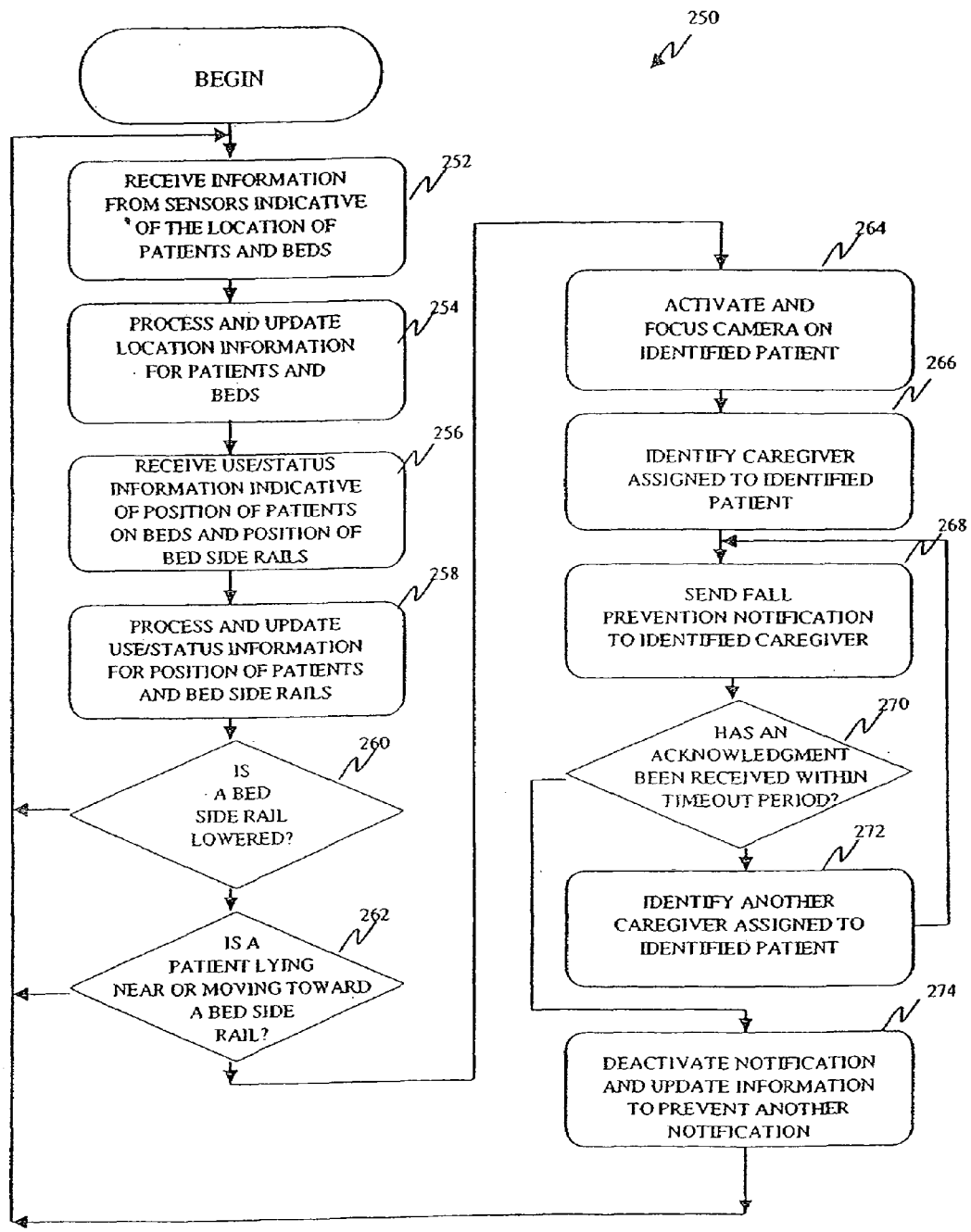
FIG. 7 illustrates an exemplary fall prevention method which is a particular embodiment of the activity based tracking method shown in FIG. 5.

Referring now to FIG. 7, there is depicted an exemplary fall prevention method 250 which is another exemplary embodiment of the ABT method 100. Experience has shown that a patient is more likely to fall out of a bed 16 if a side rail 26 of a bed 16 is in a lowered position (i.e., down). When executing the patient fall prevention method 250 of FIG. 7, the ABT system 10 generally detects the position of a patient in a bed 16 and the position of the side rails 26 of the bed 16. If ABT system 10 detects that a bed side rail 26 is in a lowered position and the patient is lying near or is moving toward the lowered bed side rail 26, then the ABT system 10 provides a caregiver with a fall prevention notification via a pocket pager or badge 12 and provides the caregiver with streaming video of the patient via a pocket pager, badge 12 or a nearby video display 28. With such information, the caregiver can assess whether corrective action is needed in order to prevent a possible fall.

The master station 34 in step 252 receives location information from badges 12 of tagged patients and badges 12 of tagged beds 16 that is indicative of the location of the tagged patients and beds 16. The master station 34 in step 254 processes the location information received in step 252 and updates location information for the tagged patients and beds 16 accordingly.

The master station 34 in step 254 receives use/status information from equipment sensors 24 of the beds 16 that is indicative of the position of a patient within a bed 16 and the position of bed side rails 26. As indicated above, the beds 16 include a patient support surface having one or more equipment sensors 24 that detect the position of a patient upon the patient support surface as disclosed in U.S. Pat. No. 6,208,250. Moreover, the bed side rails 26 include one or more equipment sensor 24 that detect the position of the side rail 26 and provide information indicative of the detected position of the bed side rail 26. In an exemplary embodiment, the bed side rails 26 are implemented as indicated in U.S. Pat. No. 6,021,533, filed on Aug. 25, 1992 and entitled "Mattress Having a Siderail Down Sensor," the disclosure of which is hereby incorporated by reference.

The master station 34 in step 258 processes the use/status information received in step 256 and updates use/status information for the beds 16 and the bed side rails 26 accordingly. More specifically, the master station in step 258 updates use/status information that indicates the position of patients on beds 16 and the position of bed side rails 26.

The master station 34 analyzes the updated location and use/status information to determine whether a patient has an increased likelihood of falling from a bed 16. More specifically, the master station 34 in step 260 determines whether a bed side rail 26 is lowered based upon the use/status information received from the bed side rails 26 in step 256. If the master station 34 determines that a bed side rail 26 is not in the lowered position (i.e., determines that the bed side rail 26 is in the raised position), then the master station 34 returns to step 252 in order to receive and process further location and use/status information. However, if the master station 34 determines that a bed side rail 26 is in the lowered position, then the master station 34 proceeds to step 262 in order to determine whether a patient is lying near or is moving toward a lowered bed side rail 26.

In step 262, the master station 34 analyzes the use/status information indicative of the position of patients within beds 16 in order to determine whether a patient is lying near or is moving toward the identified lowered bed side rails 26. If the master station 34 determines that a patient is not lying near and is not moving toward a lowered bed side rail 26, then the master station 34 returns to step 252 in order to process further location and/or use/status information.

However, if the master station 34 determines that the patient is lying near or is moving toward a lowered bed side rail 26, then the master station 34 causes actions associated with preventing the identified patient from falling from bed 16. In an exemplary embodiment, the master station 34 in step 264 activates a camera 32 located in the room of the identified patient and focuses the camera 32 on the patient if not already focused on the patient. The master station 34 in step 266 identifies which caregiver is assigned to the identified patient based upon patient assignment data that the master station 34 either maintains or has access to.

The master station in step 268 sends a fall prevention notification to the caregiver assigned to the patient lying near or moving toward the lowered bed side rail 26. More specifically, the master station 34 causes the badge 12 of the identified caregiver to provide a tactile indiction (e.g., vibrate), an audible indiction (e.g., beep), a visual indiction (e.g., blinking LED), and/or some other indication of the possible fall situation. Furthermore, the master station 34 provides the identified caregiver with streaming video of the patient via a hospital network system such as the system disclosed in U.S. Pat. Nos. 5,561,412, 5,699,038, and 5,838,223. In an exemplary embodiment, the master station 34 causes the video stream be sent to a video display 28 located near the caregiver (such as a nurse's station, hall monitor, etc.) or to a portable pager or badge 12 carried by the caregiver which has video playback capabilities.

The master station 34 in step 270 determines whether an acknowledgment was received from the caregiver within a predetermined timeout period (e.g., 30 seconds). The ABT system 10 provides various manners for the caregiver to acknowledge the fall prevention notification. For example, the ABT system 10 enables the caregiver to provide the acknowledgment by actuating a mechanism (e.g., switch, button) on their badges 12 or actuating a nearby acknowledgment mechanism (e.g., switch, button) located in various location throughout the facility such as in the patient rooms, hallways, nurses station, rest rooms, utility rooms, etc.

If the master station 34 determines that an acknowledgment was not received from the caregiver within the predetermined timeout period, then the master station 34 in step 272 identifies another caregiver assigned to the patient. The master station 34 then returns to step 268 in order to send a fall prevention notification and accompanying video stream to the newly identified caregiver. However, if the maser station 34 determines that an acknowledgment was received from the caregiver within the predetermined timeout period, then the master station 34 in step 274 deactivates the fall prevention notification and updates use/status information associated with the patient, the bed 16, and/or bed side rails 26 such that another fall prevention notification is not generated for the same patient for a predetermined time span (e.g., 5 minutes). The master station 34 then returns to step 252 in order to process further location and/or use/status information.

Figure 8:
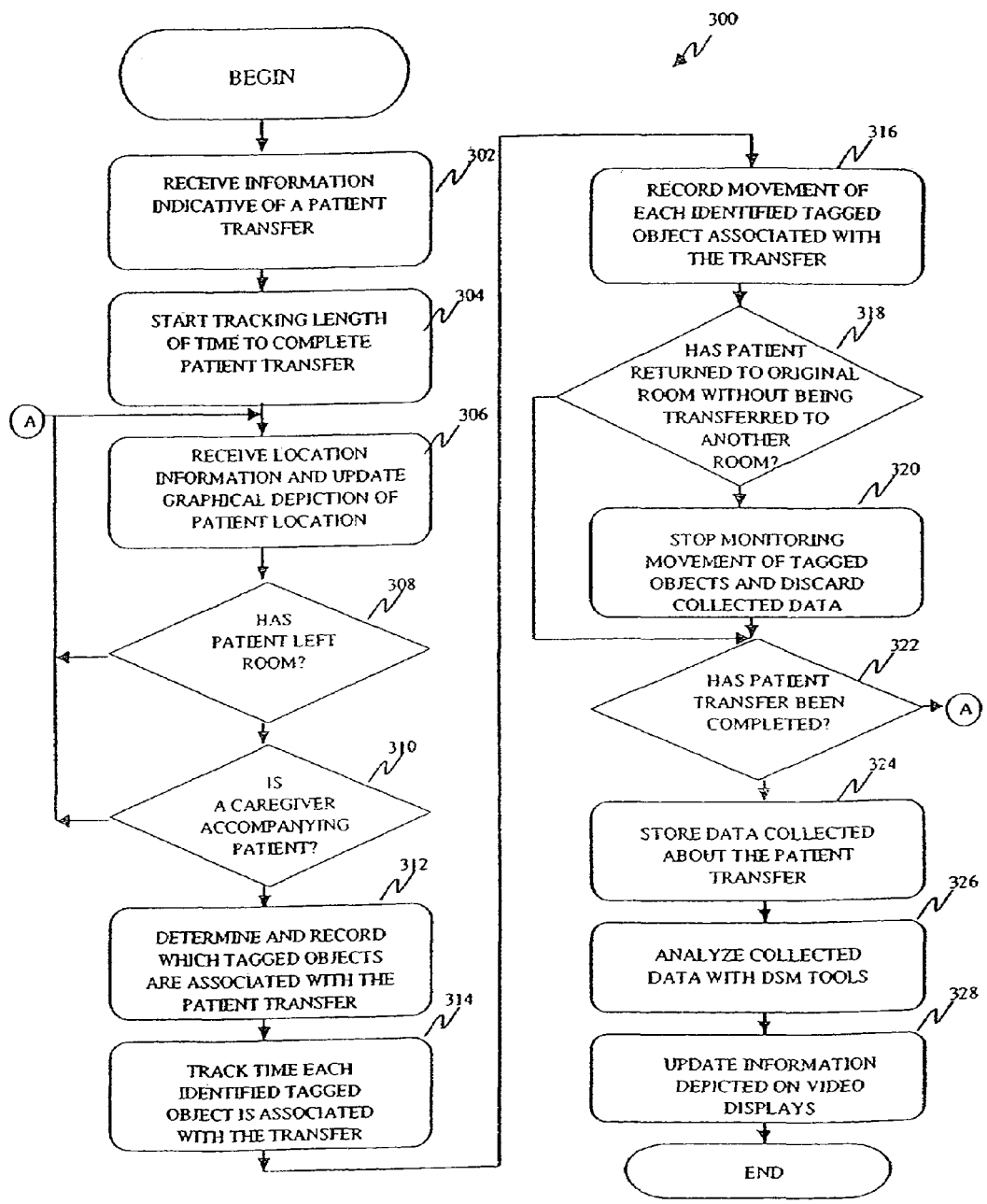
FIG. 8 illustrates an exemplary modeling simulation method which is a particular embodiment of the activity based tracking method shown in FIG. 5.

Referring now to FIG. 8, there is provided an automated method 300 for gathering information about an activity or processes in a healthcare facility and analyzing the gathered information with a simulation modeling ("SM") tool such as a dynamic simulation modeling tool or a static simulation modeling tool. SM tools enable simulations of the relationships among various processes competing for space, time and resources and enable a quantitative assessment of the impact of proposed changes. However, such SM tools require an extensive amount of data associated with the activities and processes to be simulated and analyzed. Due to the costs associated with traditional methods for obtaining sufficient information regarding activities and processes, SM tools have not been utilized in the healthcare industry. The ABT system 10 greatly reduces the cost of information gathering thus making it feasible to apply SM tools and technology to the healthcare industry.

The automated method 300 of FIG. 8 is illustrated and described in regards to gathering and analyzing information regarding the process of transferring a patient from one location to another location. However, those skilled in the art should readily appreciated that similar techniques apply to gathering and analyzing information about other processes.

In step 302, the ABT system 10 receives information indicative of the start of the process to be recorded. For example, in the case of tracking a patient transfer, the ABT system 10 receives information describing a patient transfer order that has been entered into the ABT system 10 or a clinical information system in communication with the ABT system 10 in response to a written transfer order of a physician. In an alternative embodiment, the physician directly enters the patient transfer order into the ABT system 10 or the clinical information system in communication with the ABT system 10 via a point of care computer system.

The ABT system 10 begins to record information related to the monitored activity or process. In particular, the ABT system 10 in step 304 starts tracking the length of time to complete the patient transfer. For example, the ABT system 10 records the time at which the patient transfer order was received, records the time at which the patient transfer order was written by the physician, begins a timer in response to receiving the patient transfer order, and/or utilizes some other mechanism to track the length of time to complete the patient transfer.

The ABT system 10 also tracks and records the location and movement path of tagged objects associated with the monitored activity. In particular, the ABT system 10 in step 306 monitors the location of the patient to be transferred based upon location information received from the badge 12 of the patient. Further, the ABT system 10 in step 306 continuously updates a graphical depiction of the current location of the patient upon one or more video displays 28. The ABT system 10 causes one or more video displays 28 to provide further visual indications that a transfer is taking place such as (i) causing textual information indicative of the transfer to be displayed on video displays 28 (e.g., text in the scoreboard areas), and/or (ii) causing the graphical depiction of the patient and/or the room in which the patient is to be transferred from to be altered (e.g., blink, change color).

In step 308, the ABT system 10 determines whether the patient has left the room based upon location information received from the badge 12 of the patient. If the ABT system 10 determines that the patient has not left the room, then the ABT system 10 returns to step 306 in order to further update the location of the patient. However, if the ABT system 10 determines that the patient has left the room, then the ABT system 10 in step 310 determines whether a caregiver is accompanying the patient based upon location information received by the badges 12 of the caregivers. If the ABT system 10 determines that a caregiver is not accompanying the patient, then the ABT system 10 returns to step 306 in order to further update the location of the patient.

The ABT system 10 in step 312 records which tagged objects (i.e., equipment, caregivers, etc.) are associated with the transfer of the patient. In particular, the ABT system 10 (i) determines based upon the location information received from badges 12 which caregivers are taking part in the transfer of the patient and which equipment is being transferred with the patient, and (ii) records identification information associated with such tagged objects. In an exemplary embodiment, the ABT system 10 determines which equipment is being transferred with the patient based upon information received from badges 12 of the equipment and business logic of the master station 34. Alternatively, equipment may be manually associated with a patient via terminal (not shown) of the ABT system 10, thus providing the ABT system 10 with an indication of which equipment needs to be tracked when the patient is transferred.

The ABT system 10 in step 314 tracks the length of time the identified tagged objects are involvement with the patient transfer. In particular, the ABT system 10 records the time at which each identified tagged object becomes involved with the patient transfer and records the time at which each identified tagged object becomes no longer involved with the patient transfer. Alternatively, the ABT system uses individual timers for each of the identified tagged objects or some other mechanism in order to track the objects involvement. In general, the ABT system 10 tracks the elapsed time of the patient from source (i.e., original room) to destination (i.e., new room), tracks the time of involvement of each of persons 14 involved with the transfer, and tracks the time of involvement for each piece of equipment involved with the transfer.

The ABT system 10 in step 316 records the movement of the patient, caregivers, and equipment associated with the patient transfer. The exemplary ABT system 10 periodically receives location information from the badges 12 of each tagged object on relatively short time intervals such as every 5 seconds. However, in order to reduce the amount of location information recorded, the ABT system 10 of the exemplary embodiment stores the location of each patient, caregiver, and equipment associated with the transfer on a longer time interval such as every 10 seconds. In an exemplary embodiment, the longer time interval used by ABT system 10 is user definable for each monitored activity in order to enable user selectable granularity of the movement path of the patient, caregivers, and equipment associated with a particular activity.

The ABT system 10 in step 318 determines based upon location information for the patient whether the patient has returned to the original room without being transferred to another room. If the ABT system 10 determines that the patient has been returned to the original room, then the ABT system 10 in step 320 stops monitoring the movement path and elapse times of the identified tagged objects and returns to step 306 without saving the acquired information. However, if the ABT system 10 determines that the patient has been transferred to another room, then the ABT system 10 in step 324 stores the acquired information (i.e., elapse times, movement, etc.) in a database.

The ABT system 10 then in step 326 utilizes SM tools to perform calculations on the information stored in the database. For example, the SM tools analyze the information to identify bottlenecks, resources consumed, critical paths, etc., related to transfers based upon information gathered over a predetermined time period. The ABT system 10 in step 328 updates information on the video displays 28 in order to indicate results of the SM tool analysis. For example, the ABT system 10 causes the video displays 28 to provide statistical information related to the monitored activity such as the number of transfers, the total cost of transfers, and personnel hours consumed due to transfers. Moreover, the ABT system 10 further causes the graphical depiction of rooms associated with awaiting transfers to blink, and causes the graphical depiction of hallways associated with bottlenecks in the physical transfer to blink red.

Referring now to FIG. 9, there is shown an exemplary graphical display 350 generated by the activity based tracking system 10 on video displays 28. In the exemplary embodiment, the exemplary graphical display 350 is implemented as a MedModel application executing on the master station 34. MedModel is a software tool of ProModel Corporation which is generally used for simulation modeling of healthcare facilities. The graphical display 350 includes a floor layout 352 and a scoreboard status 354. The floor layout 352 depicts the physical features of the facility (i.e., location of walls, rooms, doorways, etc.) and the location of tagged objects (e.g., beds 16, ventilators 18, persons 14). As indicated above, the master station 34 causes the floor layout 352 to provides visual indications of monitored activities (e.g., causes rooms, persons 14, and/or equipment associated with a monitored activity to be highlighted, to be depicted in a different color, or to blink on and off.)

The scoreboard status 354 generally provides pseudo-realtime statistics and other information for the facility and activities monitored in the facility. For example, the master station 34 as a result of monitoring patient transfers displays the total number of patient transfers, the total cost of patient transfers, personnel hours consumed due to patient transfers, and/or other statistical information associated with patient transfers over a certain time period.

While the invention has been illustrated and described in detail in the drawings and foregoing description, such illustration and description is to be considered as exemplary and not restrictive in character, it being understood that only exemplary embodiments have been shown and described and that all changes and modifications that come within the spirit of the invention and the attached claims are desired to be protected.

What is claimed is:

1. A system for tracking an activity in a healthcare environment, including:
   a master station having a processor, a memory coupled to the processor, and a transceiver coupled to the processor;
   a plurality of badges adapted for coupling to objects, each badge having a unique ID and including a transmitter for transmitting the badge ID; and
   a plurality of sensors disposed throughout the environment, each sensor having a unique ID that relates the sensor to a location within the environment, and including a transceiver for receiving badge IDs from badges located near the sensor and transmitting the badge IDs and the sensor ID to the master station transceiver, the master station processor determining the location of an object from the received badge ID and sensor ID by identifying the badge associated with the object, relating the sensor ID to the location of the sensor, and storing object location information in the memory;
   each of the badges further including a displacement sensor that generates signals indicating movement of the object coupled to the badge and a direction of the movement, the badge transceivers transmitting the signals for receipt by the sensor transceivers, the sensor transceivers forwarding displacement information representing the signals to the master station, the master station processor using the displacement information to update the stored object location information.

2. The system of claim 1 wherein the displacement sensor includes a speedometer.

3. The system of claim 1 wherein the master station updates the stored object location information of an object by computing a distance traveled and a direction traveled based on the signals from the displacement sensor associated with the object and modifying a last known location of the object by the distance and direction traveled by the object.

4. The system of claim 1 wherein the master station memory includes data representing physical characteristics of the environment.

5. The system of claim 1 wherein each badge transceiver transmits displacement samples at intervals that vary depending upon the rate of movement of the badge.

6. The system of claim 1 wherein the master station causes the plurality of sensors to transmit acknowledgement signals to badges that transmit object location information and displacement information, thereby providing the transmitting badges an indication that the object location information and displacement information was received by the master station.

7. The system of claim 1 wherein the master station transceiver is coupled to the sensors by a computer network.

8. The system of claim 1 further including a field generator for providing a reference field from which the displacement sensors generate the signals indicating the direction of the movement.

9. The system of claim 1 wherein the plurality of badges and the plurality of sensors include anti-collision circuitry to permit substantially simultaneous communications between multiple badges and a sensor.

10. The system of claim 1 wherein the sensors include short range sensors and long range sensors.

11. The system of claim 10 wherein the master station uses the object location information from the short range sensors to increase the accuracy of the object location information.

12. The system of claim 10 wherein the sensors include equipment sensors that provide status information associated with the equipment.

13. The system of claim 12 wherein the master station transceiver is coupled to the equipment sensors by a computer network.

14. The system of claim 12 wherein the master station transceiver includes a wireless transmitter and a wireless receiver for wirelessly communicating with the sensors and the equipment sensors.

15. The system of claim 12 wherein the status information includes an indication of whether the equipment is in use.

16. The system of claim 12 wherein the equipment sensors are associated with patients, the status information being time-stamped to permit correlation of patient billing to actual equipment usage.

17. The system of claim 1 wherein each displacement sensor includes an orientation sensor that provides signals indicating an orientation of the badge relative to a reference field.

18. The system of claim 17 wherein the orientation sensors include tilt correction circuitry.

19. The system of claim 1 further including displays coupled to the master station to receive object location information and provide a graphical display of the locations of objects within the environment.

20. The system of claim 19 wherein the displays are coupled to cameras located in the environment to provide video of objects, the displays being operable to display the video.

21. The system of claim 20 wherein the displays are portable.

22. The system of claim 1 wherein the master station determines a movement path and a location of an object associated with a badge based upon the received badge ID, the displacement samples, and a previously determined location of the badge.

23. The system of claim 22 wherein the master station compares the movement path to the data in the master station memory representing the physical characteristics of the environment to determine whether the movement path is consistent with available paths for movement of the object.

24. The system of claim 1 wherein the badge transmitters are RF transmitters that receive power from one of the plurality of sensors when in proximity of the sensor.

25. The system of claim 24 wherein the badges transmit the badge IDs in response to receipt of power from the sensor.

26. The system of claim 1 wherein each displacement sensor includes a motion sensor that generates a signal indicating movement of the object.

27. The system of claim 26 wherein the motion sensor signal indicates at least one of dynamic acceleration and static acceleration.

28. The system of claim 1 wherein each displacement sensor includes a direction sensor that generates a signal indicating a directional orientation of the object relative to a reference direction.

29. The system of claim 28 wherein the direction sensor signal indicates a horizontal orientation of the object relative to the reference direction.

30. The system of claim 28 wherein the direction sensor includes a three-dimensional field sensor and a pitch-and-roll sensor.

31. The system of claim 30 wherein the pitch-and-roll sensor includes a two-dimensional accelerometer.

32. The system of claim 1 wherein each of the badges includes a controller for processing the displacement sensor signals, and a memory for storing displacement samples representing the displacement sensor signals.

33. The system of claim 32 wherein the controller computes a speed of movement of the object.

34. The system of claim 32 wherein the plurality of badges transmit displacement samples at predetermined time intervals.

35. The system of claim 32 wherein the plurality of badges transmit badge IDs and any displacement samples stored in the badge memory since a prior receipt of an acknowledgement signal indicating a successful transmission of a prior displacement sample.

36. The system of claim 32 wherein the controller combines displacement samples that are temporally adjacent and do not significantly differ from one another, thereby reducing the number of displacement samples stored in the badge memory.

37. The system of claim 32 wherein the controller includes a counter for counting a number of displacement samples represented by a stored displacement sample.

38. The system of claim 32 wherein the badge controller includes a timer for time-stamping the displacement samples.

39. The system of claim 32 wherein each badge includes a battery for providing power to the badge in response to receipt of power from one of the plurality of sensors, the badge controller discontinuing battery power upon detection of a power off condition.

40. The system of claim 39 wherein the power off condition includes passage of a predetermined time period.

41. The system of claim 32 wherein the master station responds to receipt of a transmitted badge ID and a transmitted displacement sample by causing an acknowledgement signal to be sent to the badge.

42. The system of claim 41 wherein the acknowledgement signal is transmitted to the badge by a sensor transceiver.

43. The system of claim 42 wherein the controller responds to receipt of the acknowledgement signal by erasing the transmitted displacement sample from the badge memory.

44. A system for tracking an activity in a healthcare environment, including:
   a first sensor associated with a person configured to transmit a first signal indicating the location of the person;
   a second sensor associated with a piece of equipment configured to transmit a second signal indicating a condition of the equipment;
   a plurality of first transceivers for receiving the first and second signals and transmitting information representing the first and second signals; and
   a master station including a second transceiver in communication with the plurality of first transceivers for receiving the transmitted information to determine the location of the person and the condition of the equipment, the master station comparing the transmitted information to predetermined criteria and initiating an action when the transmitted information satisfies the predetermined criteria.

45. The system of claim 44 wherein the plurality of first transceivers include short range transceivers and long range transceivers.

46. The system of claim 44 wherein the second transceiver is coupled to the plurality of first transceivers by a computer network.

47. The system of claim 44 wherein the second transceiver includes a wireless transmitter and a wireless receiver for wirelessly communicating with the plurality of first transceivers.

48. The system of claim 44 wherein the master station causes the plurality of first transceivers to transmit acknowledgement signals to the first sensor, thereby providing the first sensor an indication that the transmitted information was received by the master station.

49. The system of claim 44 wherein the second sensor is one of a current sensor, a voltage sensor, and a power sensor.

50. The system of claim 44 further including a third sensor associated with the piece of equipment configured to transmit a third signal indicating the location of the equipment, the transmitted information from the plurality of first transceivers also representing the third signal from which the master station determines the location of the equipment.

51. The system of claim 44 wherein the action includes activation of a camera located in proximity to the person to obtain video of the person, the camera transmitting the video to a display for viewing by a caregiver.

52. The system of claim 44 further including displays coupled to the master station to receive person location information and provide a graphical display of a location of the person within the environment.

53. The system of claim 52 wherein the displays are coupled to cameras located in the environment to provide video of the person, the displays being operable to display the video.

54. The system of claim 52 wherein the displays are portable.

55. The system of claim 44 wherein the first sensor includes an RF transmitter that receives power from one of the plurality of first transceivers when in proximity of the first transceiver.

56. The system of claim 55 wherein the first sensor transmits the first signal in response to receipt of power from the first transceiver.

57. The system of claim 44 wherein the condition is whether the equipment is in use.

58. The system of claim 57 wherein the second sensor is associated with a patient, the second signal being time-stamped to permit correlation of patient billing to actual equipment usage.

59. The system of claim 44 wherein the person is a caregiver and the second sensor is associated with a hand-washing device, the second signal indicating an in-use condition of the handwashing device.

60. The system of claim 59 wherein the predetermined criteria includes a hygiene policy, the action including generating a record of one of compliance and noncompliance with the hygiene policy.

61. The system of claim 44 wherein the first signal indicates the person's location relative to a side rail of a bed, and the second signal indicates an in-use condition of a ventilator.

62. The system of claim 61 wherein the predetermined criteria includes an extubation event wherein the person is contacting the side rail and the ventilator is in use, the action including notifying a caregiver of the extubation event.

63. The system of claim 44 wherein the master station confirms completion of the action upon receipt of an acknowledgment signal.

64. The system of claim 63 wherein a caregiver generates the acknowledgement signal by actuating a switch.

65. The system of claim 44 wherein the first signal indicates the person's position on a bed, and the second signal indicates a whether a side rail of the bed is in a lowered position.

66. The system of claim 65 wherein the predetermined criteria includes a potential fall condition wherein the person's position is one of near and moving toward the side rail and the side rail is in the lowered position, the action including notifying a caregiver of the potential fall condition.

67. The system of claim 66 wherein the action includes activation of a camera located in proximity to the person to obtain video of the person, the camera transmitting the video to a display for viewing by a caregiver.

68. A system for tracking activities in a healthcare environment, including:
a plurality of transmitters adapted to be coupled to a corresponding plurality of movable objects, each transmitter outputting a transmitter ID signal that identifies the corresponding object;
a plurality of sensors disposed at a corresponding plurality of locations throughout the healthcare environment, each sensor including a transceiver for receiving the transmitter ID signals and transmitting information including the received transmitter ID signals and a sensor ID signal indicating the location of the sensor; and
a master station in communication with the plurality of sensors, the master station including a receiver for receiving the information transmitted by the sensors, a processor for determining from the received information the location of each of the plurality of objects, a timer for monitoring the length of time objects remain in locations, and a memory for storing data indicating movement of the plurality of objects into and out of locations and the time such movement occurred;
wherein the master station automatically accumulates the data from the sensors, associates portions of the data with particular activities, and generates statistical analyses of the data associated with the particular activities to identify characteristics associated with the particular activities.

69. The system of claim 68 wherein the master station automatically detects an event associated with a beginning of a particular activity.

70. The system of claim 68 further including a display, the master station generating a graphical representation of the movement of the plurality of objects from the data in the memory for display on the display.

71. The system of claim 68 wherein the statistical analyses include information representing a number of objects involved in a particular activity, a time duration of involvement corresponding to each of the number of objects, and a cost associated with the particular activity.

72. The system of claim 68 wherein the sensors include short range sensors and long range sensors.

73. The system of claim 68 wherein the master station receiver is coupled to the plurality of sensor transceivers by a computer network.

74. The system of claim 68 wherein the master station receiver wirelessly receives the transmitted information.

75. The system of claim 68 wherein the plurality of transmitters and the plurality of sensors include anti-collision circuitry to permit substantially simultaneous communications between multiple transmitters and a sensor.

76. The system of claim 68 wherein each of the plurality of transmitters is an RF transmitter that receives power from one of the plurality of sensors when in proximity of the sensor.

77. The system of claim 76 wherein the plurality of transmitters transmit the transmitter ID signals in response to receipt of power from the sensor.

78. The system of claim 68 wherein each of the plurality of transmitters further includes a displacement sensor that generates signals indicating movement of the object coupled to the transmitter and a direction of the movement, the transmitter transmitting the signals for receipt by the plurality of sensor transceivers, the sensor transceivers forwarding displacement information representing the signals to the master station, the master station processor using the displacement information to update the data stored in the master station memory.

79. The system of claim 78 further including a field generator for providing a reference field from which the displacement sensors generate the signals indicating the direction of the movement.

80. The system of claim 78 wherein each displacement sensor includes an orientation sensor that provide signals indicating an orientation of the badge relative to a reference field.

81. The system of claim 78 wherein each displacement sensor includes a motion sensor that generates a signal indicating movement of the corresponding object.

82. The system of claim 78 wherein the displacement sensor includes a speedometer.

83. The system of claim 78 wherein the master station stores information representing the locations of the objects, and updates the stored object location information of an object by computing a distance traveled and a direction traveled based on the signals from the displacement sensor associated with the object and modifying a last known location of the object by the distance and direction traveled by the object.

84. The system of claim 78 wherein each of the plurality of transmitters includes a controller for processing the displacement sensor signals, and a memory for storing displacement samples representing the displacement sensor signals.

85. The system of claim 84 wherein the controller computes a speed of movement of the object.

86. A system for tracking an activity in a healthcare environment, including:
   means for collecting activity information including means for processing the information, means for storing the processed information, and means for transmitting and receiving signals;
   a plurality of means respectively coupled to a plurality of objects for transmitting unique transmitter IDs respectively associated with the objects;
   a plurality of means disposed throughout the environment for sensing transmissions from the plurality of transmitting means, each sensing means having a unique sensor ID that relates the sensing means to a location within the environment, and including means for receiving transmitter IDs from transmitting means located near the sensing means and transmitting the transmitter IDs and the sensor ID to the activity information collection means, the processing means determining the location of an object from the received transmitter ID and sensor ID by identifying the transmitting means associated with the object, relating the sensor ID to the location of the sensing means, and storing object location information in the storing means;
   each of the transmitting means further including means for sensing displacement, the displacement sensing means generating signals indicating movement of the object coupled to the transmitting means and a direction of the movement, the transmitting means transmitting the signals for receipt by the sensing means, the sensing means forwarding displacement information representing the signals to the activity information collection means, the activity information collection means using the displacement information to update the stored object location information, and further including means for timing a length of time an object remain in a location, means for associating portions of the stored object location information with particular activities, and means for generating statistical analyses of the portions of stored object location information associated with the particular activities to identify inefficiencies associated with the particular activities.

87. The system of claim 44 wherein the master station determines the location of the person and the condition of the equipment from the transmitted information.

* * * * *